US010869597B2

(12) United States Patent
Patterson et al.

(10) Patent No.: US 10,869,597 B2
(45) Date of Patent: Dec. 22, 2020

(54) AIR REMOVAL AND FLUID TRANSFER FROM A CLOSED SYSTEM

(71) Applicant: Lantos Technologies, Inc., Wakefield, MA (US)

(72) Inventors: Shawn M. Patterson, Wakefield, MA (US); Steve Schmidt, Wakefield, MA (US); Mac Andrew Dougan, Wakefield, MA (US); Brian Connolly, Wakefield, MA (US); Manas Menon, Wakefield, MA (US); Lynn Ihlenfeldt, Wakefield, MA (US)

(73) Assignee: LANTOS TECHNOLOGIES, INC., Wilmington, MA (US)

( * ) Notice: Subject to any disclaimer, the term of this patent is extended or adjusted under 35 U.S.C. 154(b) by 518 days.

(21) Appl. No.: 14/951,408

(22) Filed: Nov. 24, 2015

(65) Prior Publication Data
US 2016/0150949 A1     Jun. 2, 2016

Related U.S. Application Data

(60) Provisional application No. 62/084,510, filed on Nov. 25, 2014.

(51) Int. Cl.
*A61B 1/227* (2006.01)
*A61B 1/015* (2006.01)
(Continued)

(52) U.S. Cl.
CPC ............ *A61B 1/2275* (2013.01); *A61B 1/015* (2013.01); *A61B 5/0084* (2013.01);
(Continued)

(58) Field of Classification Search
CPC ....... A61B 1/2275; A61B 1/015; A61B 1/227; A61B 5/0084; A61B 5/1076; A61B 5/1079; A61B 5/6817
(Continued)

(56) References Cited

U.S. PATENT DOCUMENTS 3,790,653 A    2/1974   Barkey et al.
4,643,733 A    2/1987   Becker
(Continued)

FOREIGN PATENT DOCUMENTS

CA       2840602 A1    1/2013
CN    102177733 A      9/2011
(Continued)

OTHER PUBLICATIONS

PCT/US15/62464, "International Application Serial No. PCT/US15/62464, International Preliminary Report on Patentability, dated May 30, 2017", Lantos Technologies Inc., 5 pages.
(Continued)

*Primary Examiner* — Catherine M Voorhees
*Assistant Examiner* — Roland Dinga
(74) *Attorney, Agent, or Firm* — GTC Law Group PC & Affiliates

(57) ABSTRACT

Methods, apparatus, and systems are provided for scanning and measuring an anatomical cavity. An apparatus may include an absorbing medium assembly that is fluidly connected to an earpiece and configured to provide an absorbing medium to the earpiece. The absorbing medium assembly may include a medium container with a gas trap, as well as a tube fluidly connected to the medium container. The gas trap may be located at a top portion of the medium container. The tube may be coupled to the top portion or a bottom portion of the medium container. The system may include a dip tube disposed inside the medium container when the tube of the absorbing medium assembly couples to a top portion of the medium container. A gas relief valve configured to enable gas to escape may also be present in the apparatus.

22 Claims, 21 Drawing Sheets

(51) Int. Cl.
  *A61B 5/00*   (2006.01)
  *A61B 5/107*  (2006.01)

(52) U.S. Cl.
  CPC .......... *A61B 5/1076* (2013.01); *A61B 5/1079* (2013.01); *A61B 5/6817* (2013.01); *A61B 1/227* (2013.01)

(58) Field of Classification Search
  USPC ........................................................ 600/476
  See application file for complete search history.

(56) References Cited

U.S. PATENT DOCUMENTS

| | | | |
|---|---|---|---|
| 5,100,587 A | | 3/1992 | Clough et al. |
| 5,504,316 A | | 4/1996 | Bridgelall et al. |
| 5,829,350 A | | 11/1998 | Muchi et al. |
| 6,001,059 A | * | 12/1999 | Elliott ................ A61B 1/00087 600/184 |
| 8,032,337 B2 | | 10/2011 | Deichmann et al. |
| 8,047,207 B2 | | 11/2011 | Perez et al. |
| 8,107,086 B2 | | 1/2012 | Marini et al. |
| 8,384,916 B2 | | 2/2013 | Hart et al. |
| 8,840,566 B2 | | 9/2014 | Seibel et al. |
| 8,845,526 B2 | | 9/2014 | Hart et al. |
| 9,291,565 B2 | | 3/2016 | Hart et al. |
| 9,592,100 B2 | | 3/2017 | Olson et al. |
| 10,122,989 B2 | | 11/2018 | Fei et al. |
| 2003/0164952 A1 | | 9/2003 | Deichmann et al. |
| 2004/0107080 A1 | | 6/2004 | Deichmann et al. |
| 2005/0191451 A1 | | 9/2005 | Osika et al. |
| 2007/0106012 A1 | | 5/2007 | Matyjaszewski et al. |
| 2008/0027358 A1 | | 1/2008 | Gregersen et al. |
| 2008/0058629 A1 | | 3/2008 | Seibel et al. |
| 2009/0171196 A1 | | 7/2009 | Hauck et al. |
| 2009/0245530 A1 | * | 10/2009 | Keady .................... A61F 11/08 381/72 |
| 2009/0289938 A1 | | 11/2009 | Paulsen |
| 2009/0296980 A1 | | 12/2009 | Yi |
| 2010/0019170 A1 | | 1/2010 | Hart et al. |
| 2010/0039534 A1 | | 2/2010 | Hart et al. |
| 2010/0042002 A1 | | 2/2010 | Hart et al. |
| 2010/0168562 A1 | | 7/2010 | Zhao et al. |
| 2010/0296664 A1 | | 11/2010 | Burgett et al. |
| 2011/0009702 A1 | | 1/2011 | Morishita et al. |
| 2011/0076608 A1 | | 3/2011 | Bergemann et al. |
| 2011/0144480 A1 | | 6/2011 | Lu et al. |
| 2011/0235843 A1 | * | 9/2011 | Keady .................... A61F 11/10 381/380 |
| 2011/0290005 A1 | | 12/2011 | Hart et al. |
| 2012/0327426 A1 | | 12/2012 | Hart et al. |
| 2013/0002426 A1 | | 1/2013 | Hart et al. |
| 2013/0002824 A1 | | 1/2013 | Hart et al. |
| 2013/0027516 A1 | | 1/2013 | Hart et al. |
| 2013/0078555 A1 | | 3/2013 | Orihara et al. |
| 2013/0261655 A1 | | 10/2013 | Drasler et al. |
| 2014/0272221 A1 | | 9/2014 | Forsyth et al. |
| 2014/0275974 A1 | | 9/2014 | Samuels |
| 2014/0276005 A1 | | 9/2014 | Forsyth et al. |
| 2014/0276105 A1 | * | 9/2014 | De Brouchoven .. A61B 5/0071 600/476 |
| 2014/0330133 A1 | | 11/2014 | Stern |
| 2015/0017779 A1 | | 1/2015 | Kim |
| 2015/0036146 A1 | | 2/2015 | Staloff |
| 2017/0104977 A1 | | 4/2017 | Fei et al. |
| 2018/0178419 A1 | | 6/2018 | Fei et al. |
| 2018/0319047 A1 | | 11/2018 | Fei et al. |
| 2019/0014309 A1 | | 1/2019 | Fei et al. |

FOREIGN PATENT DOCUMENTS

| | | |
|---|---|---|
| CN | 103974183 A | 8/2014 |
| CN | 104333826 A | 2/2015 |
| CN | 104796806 A | 7/2015 |
| CN | 104936054 A | 9/2015 |
| JP | H08243262 A | 9/1996 |
| WO | 2012115863 A2 | 8/2012 |
| WO | 2013002935 A1 | 1/2013 |
| WO | 2013003416 A2 | 1/2013 |
| WO | 2014145058 A1 | 9/2014 |
| WO | 2014145077 A1 | 9/2014 |
| WO | WO-2014/145026 A2 | 9/2014 |
| WO | 2015017779 A1 | 2/2015 |
| WO | 2016086005 A1 | 6/2016 |
| WO | 2017062868 A1 | 4/2017 |
| WO | 2017062868 A8 | 4/2017 |
| WO | 2018118772 A9 | 6/2018 |

OTHER PUBLICATIONS

PCT/US15/62464, "International Application Serial No. PCT/US15/62464, International Search Report and Written Opinion dated Mar. 31, 2016", Lantos Technologies Inc., 7 pages.
U.S. Appl. No. 16/132,055, filed Sep. 14, 2018, Pending, Robert J. Fei.
WelchAllyn CompacVideo Otoscope Model 23120 (NTSC) and 23120P (PAL), Operating Instruction Manual, 2000, 16 pages.
"International Search Report and Written Opinion dated Sep. 11, 2014 for PCT application No. PCT/US2014/029662", 6 pages.
"International Search Report and Written Opinion dated Jul. 31, 2014 for PCT application No. PCT/US2014/029712", 6 pages.
"International Search Report and Written Opinion dated Aug. 7, 2014 for PCT application No. PCT/US2014/029738", 6 pages.
Park, "3D scan designs headphones just for you", [retrieved Dec. 19, 2016], http://www.unitedsciences.com/151-2, Jan. 10, 2015, 2 pages.
PCT/US16/56132, "International Application Serial No. PCT/US16/56132, International Preliminary Report on Patentability and Written Opinion dated Apr. 19, 2018", Lantos Technologies Inc., 7 Pages.
PCT/US16/56132, "International Application Serial No. PCT/US16/56132, International Search Report and Written Opinion dated Jan. 26, 2017", Lantos Technologies, Inc., 8 pages.
PCT/US17/67010, "International Application Serial No. PCT/US17/67010, International Search Report and the Written Opinion dated Mar. 9, 2018.", Lantos Technologies Inc., 11 pages.
PCT/US2014/029662, "International Application Serial No. PCT/US2014/029662, International Preliminary Report on Patentability dated Sep. 24, 2015", 5 pages.
PCT/US2014/029712, "International Application Serial No. PCT/US2014/029712, International Preliminary Report on Patentability dated Sep. 24, 2015", 5 pages.
PCT/US2014/029738, "International Application Serial No. PCT/US2014/029738 International Preliminary Report on Patentability dated Sep. 24, 2015", 5 pages.
16854493.0, "International Application Serial No. 16854493.0, Extended European Search Report dated May 17, 2019", Lantos Technologies, Inc., 10 pages.
PCT/US17/67010, "International Application Serial No. PCT/US17/67010, International Preliminary Report on Patentability dated Jul. 4, 2019", Lantos Technologies, Inc., 8 pages.
17885270.3, "European Application Serial No. 17885270.3, Extended European Search Report dated May 19, 2020", Lantos Technologies, Inc., 8 pages.

* cited by examiner

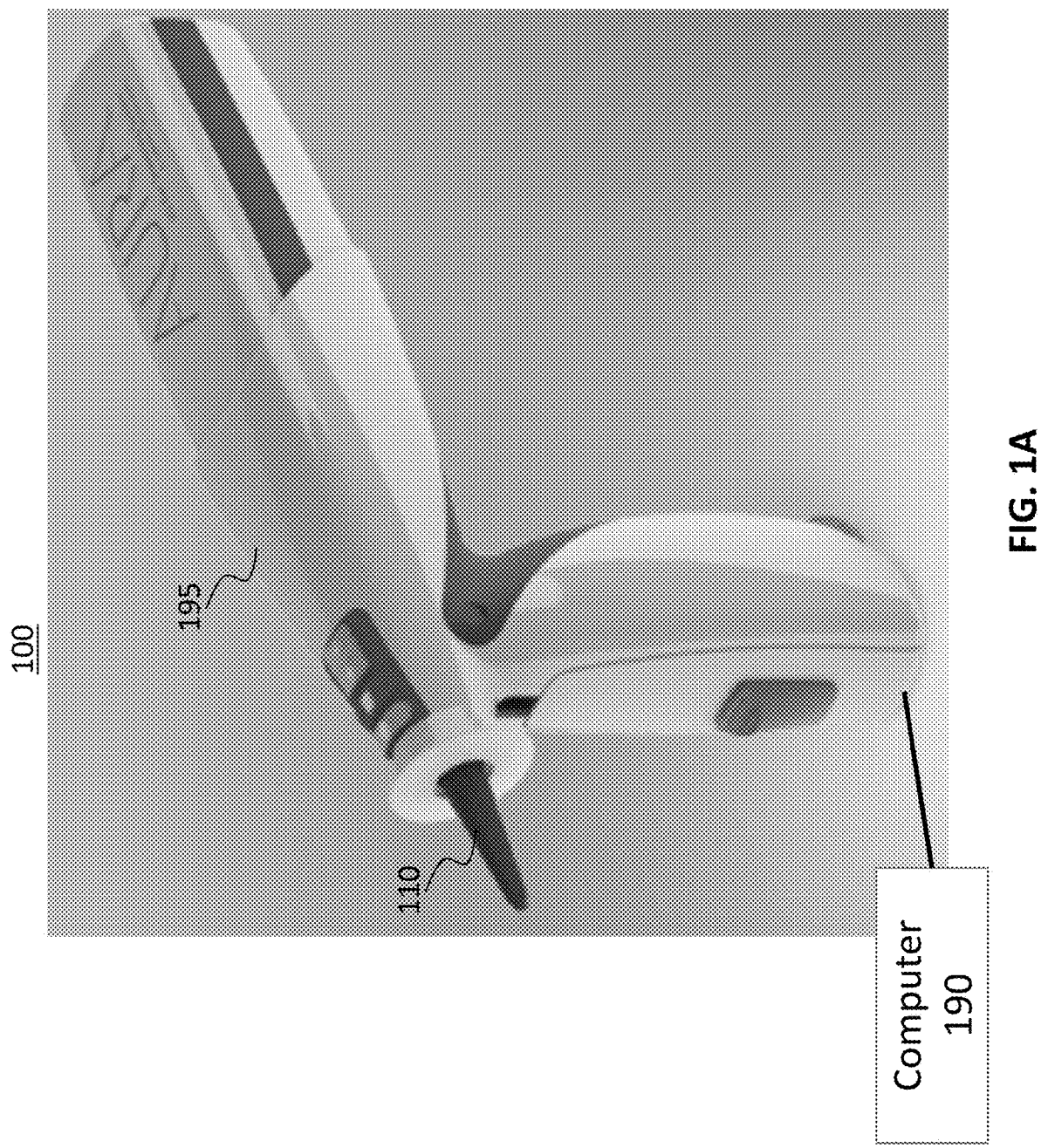

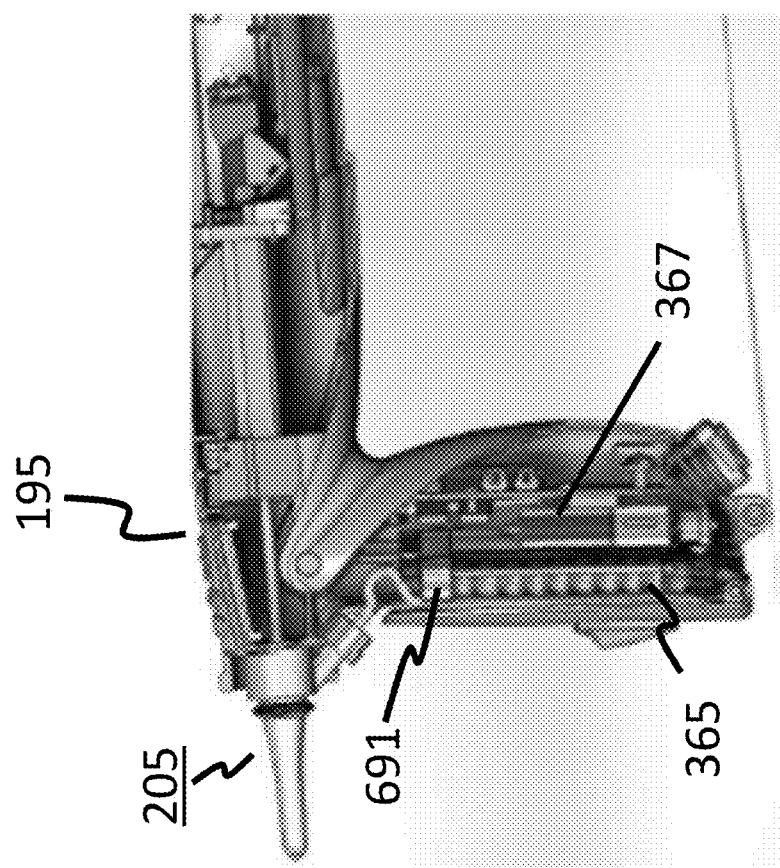

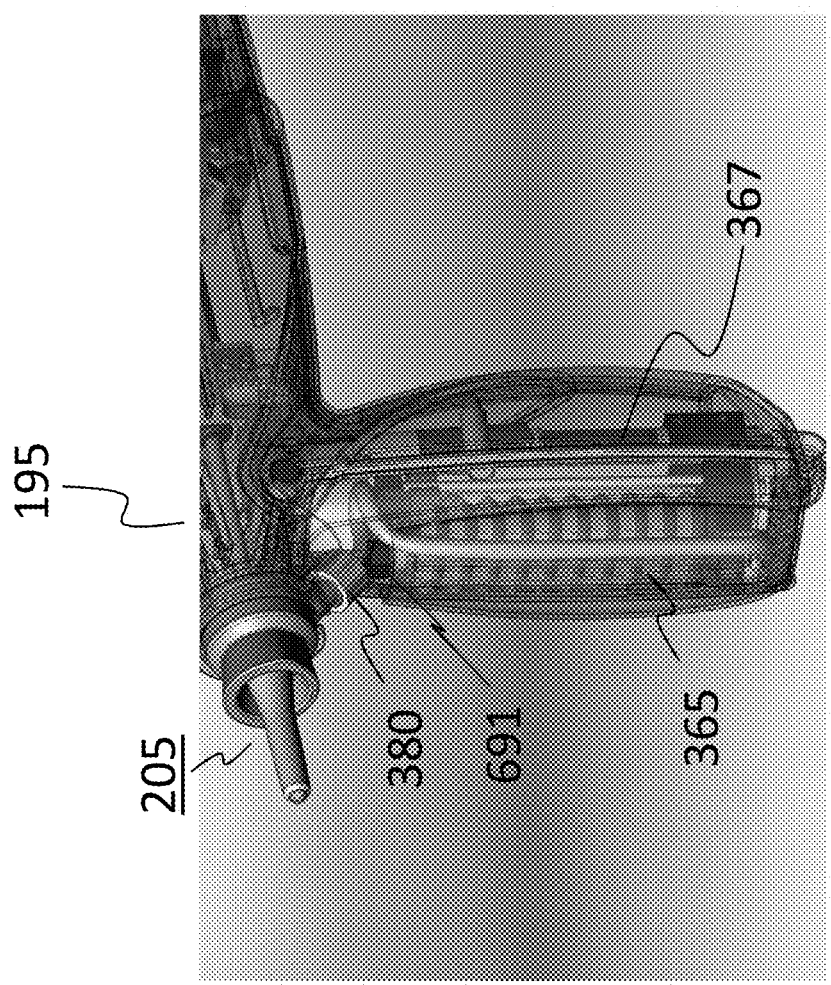

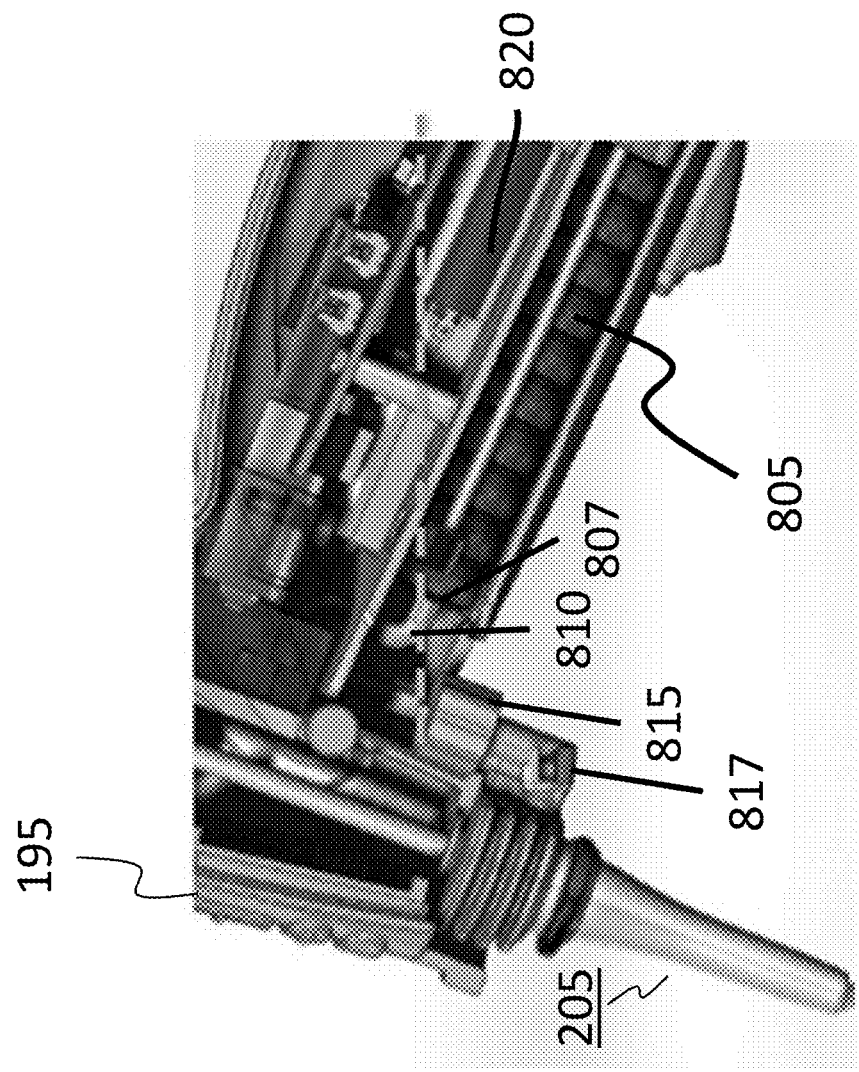

AIR REMOVAL AND FLUID TRANSFER FROM A CLOSED SYSTEM

CROSS-REFERENCE TO RELATED APPLICATION

This application claims priority to U.S. Provisional Application Ser. No. 62/084,510, filed Nov. 25, 2014 and titled "Air Removal and Fluid Transfer From a Closed System," the disclosure of which is hereby incorporated by reference herein.

FIELD

The subject matter described herein relates to systems for scanning and measuring cavities, particularly anatomical cavities such as a human ear canal.

BACKGROUND

Devices can be created to fit into anatomical cavities, such as the human ear canal. When creating devices for insertion into anatomical cavities, having a comfortable and snug fit between a device and the cavity into which it is placed can increase the likelihood that a user will wear the device, as well as enhance the performance of the device.

Traditional methods of scoping and measuring sensitive cavities, such as anatomical cavities, include creating impressions of the cavity. Creating or taking an impression includes injecting a material into the cavity. The material is allowed to harden and conform to the shape of the cavity, and then the material is extracted from the cavity. An impression created this way can cause complications or pain when the impression material is injected into the cavity, when the material is hardening, or when the impression is extracted. The impression process, including hardening and extraction, can exert pressure on the walls of the cavity in a painful or damaging way.

SUMMARY

Methods, systems, and apparatus, are provided for transferring fluids used in systems for scoping and measuring anatomical cavities.

In some example embodiments, there may be provided an apparatus including an absorbing medium assembly configured to fluidly connect to an earpiece and provide an absorbing medium to the earpiece, in which the absorbing medium assembly includes a medium container with a gas trap, as well as a tube fluidly connected to the medium container.

In some implementations, the above-noted aspects may further include additional features described herein including one or more of the following. The earpiece may further include an inflatable membrane, a main body, and a scanning element to scan an ear. The apparatus may further include a compressor coupled to the absorbing medium assembly to compress and to expand the medium container to enable removal of one or more volumes of gas from at least the earpiece in some implementations. The medium container may be a bellows container that enables collapse in a controlled manner when compressed by the compressor. In some implementations, the first end of the tube may couple to a bottom portion of the medium container. The first end of the tube may couple to a top portion of the medium container in some implementations. When a first end of the tube couples to a top portion of the medium container, the apparatus may include a dip tube disposed inside the medium container to draw absorbing medium from the medium container and to enable avoidance of one or more volumes of gas within the medium container. In some embodiments of the apparatus that include a dip tube, the dip tube may be fluidly connected to the tube of the absorbing medium assembly. The gas trap may be located at a top portion of the medium container. The apparatus may further include a gas relief valve that is configured to enable gas to escape from the apparatus. In some embodiments, the gas relief valve may couple the earpiece and the absorbing medium assembly. The gas relief valve may be located adjacent to the gas trap in some implementations of the apparatus. The gas relief valve may include a least one of a semi-permeable surface or a valve.

In some example embodiments, there may be provided a method including moving, by an absorbing medium assembly, absorbing medium from a medium container into an inflatable membrane of an earpiece. In the method, the absorbing medium assembly may be configured to fluidly connect to the earpiece and provide an absorbing medium to the earpiece, and the absorbing medium assembly may include a medium container with a gas trap and a tube fluidly connected to the medium container.

In some implementations, the above-noted aspects may further include additional features described herein including one or more of the following. The method may further include moving, by the absorbing medium assembly, the absorbing medium from the medium container into the inflatable membrane of the earpiece to enable one or more volumes of gas to accumulate in the gas trap. Some implementations of the method may include moving, by the absorbing medium assembly, the absorbing medium, after at least some removal of the one or more volumes of gas from the medium container, into the inflatable membrane of the earpiece to enable inflation of the inflatable membrane. The method may further include scanning an ear. In some implementations, the earpiece may further include a main body and a scanning element to scan an ear. A compressor may be coupled to the absorbing medium assembly to compress and to expand the medium container to enable removal of one or more volumes of gas from at least the earpiece. The gas trap may be located at a top portion of the medium container in some implementations. A gas relief valve may be included that is configured to enable gas to escape from a system, in which the system includes the absorbing medium assembly and the earpiece. The gas relief valve may couple the earpiece and the absorbing medium assembly. The gas relief valve may be located adjacent to the gas trap. The gas relief valve may include at least one of a semi-permeable surface or a valve in some implementations.

The above-noted aspects and features may be implemented in systems, apparatus, methods, and/or articles depending on the desired configuration. The details of one or more variations of the subject matter described herein are set forth in the accompanying drawings and the description below. Features and advantages of the subject matter described herein will be apparent from the description and drawings, and from the claims.

DESCRIPTION OF DRAWINGS

In the drawings,

FIG. 1A depicts an example of a system including a three-dimensional (3D) scanner having an inflatable membrane;

FIGS. 6A and 6B depict further views of the 3D scanner shown in FIGS. 2A, 4, and 5;

FIG. 7A depicts an example implementation of a 3D scanner, including a housing enclosing a bellows fluid container and a compression assembly;

FIGS. 8A and 8B depict an example implementation of a 3D scanner with an alternative configuration of the fluid container;

Figure 1B:
FIG. 1B depicts an example 3D rendering of a cavity formed based on scanner data collected and processed by the 3D scanner system of FIG. 1A.

Like labels are used to refer to same or similar items in the drawings.

DETAILED DESCRIPTION

Injection of materials into sensitive cavities, such as anatomical cavities, may, as noted, cause pain and/or damage to the cavity. Alternative methods for scoping and measuring such cavities may include scanning techniques that utilize light. Described herein are methods, apparatus, and systems for scanning techniques for scoping and measuring anatomical cavities, including the human ear canal. The methods, apparatus, and systems described may include the use of disposable components in closed systems and the removal or sequestering of air and other gases from these closed systems.

FIG. 1A depicts a scanning system 100 including an inflatable membrane 110, in accordance with some example implementations. The system 100 and accompanying software may generate three-dimensional (3D) scans of a cavity, such as an ear cavity.

System 100 may include a 3D scanner 195 including inflatable membrane 110 and a processor 190, such as a computer. The processor 190 may process scanner data generated by 3D scanner 195 during a scan of the cavity. The processor 190 may form an output, such as a 3D impression of the scanned cavity. FIG. 1B depicts an example of a 3D surface formed by processor 190 based on scan data provided by 3D scanner 195. The 3D surface may model the cavity being scanned, such as an ear cavity, and this 3D surface may be provided to a manufacturer, 3D printer, and the like to form an object. In the case of the ear, the object may be an earpiece.

Figure 1C:
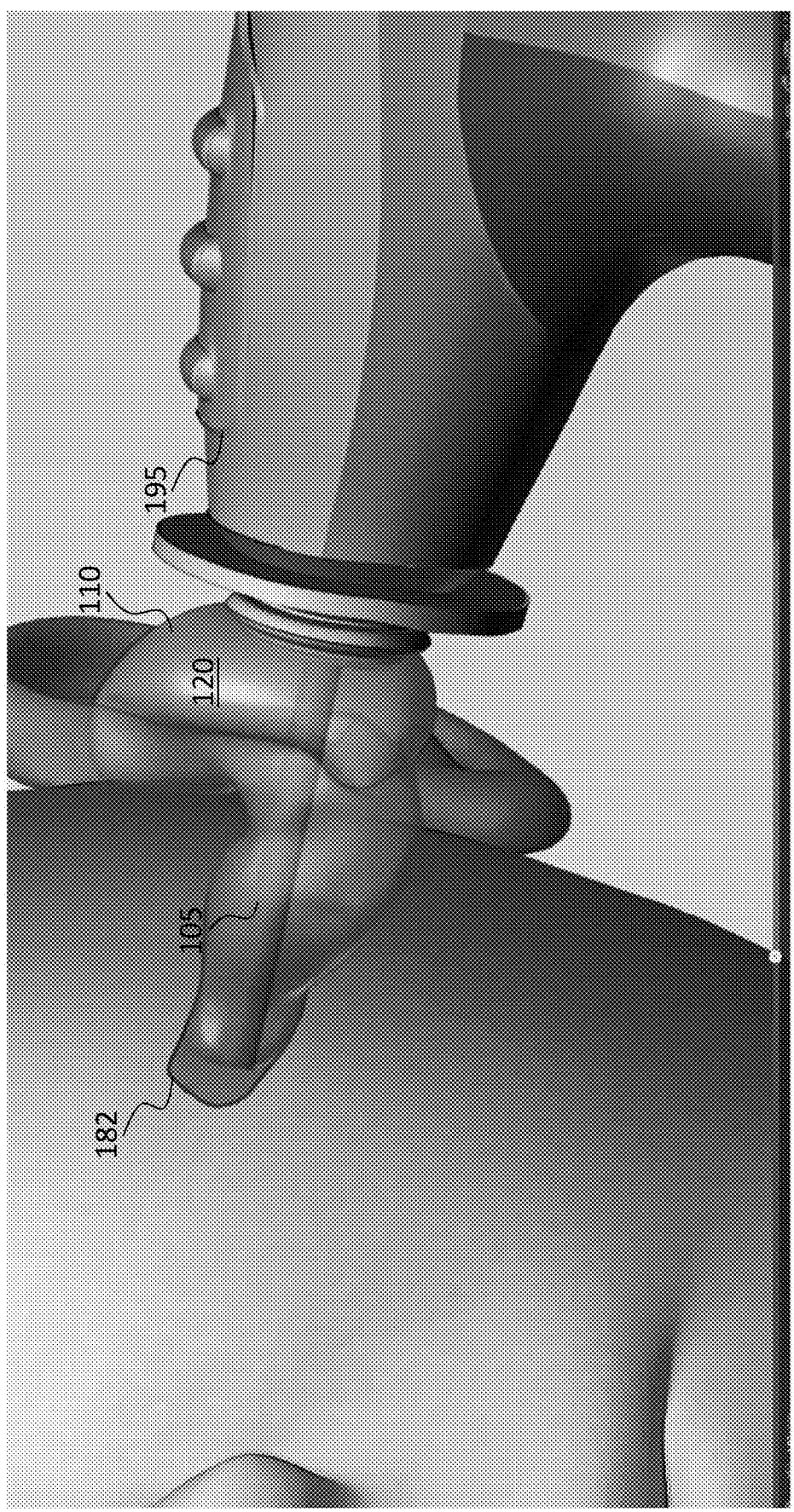
FIGS. 1C-D depict examples of a system including a 3D scanner having an inflatable membrane.

FIG. 1C depicts a portion of 3D scanner 195 after being inserted into an ear cavity 182 and after a medium 120 is used to expand the interior of the inflatable membrane 110, so that the inflatable membrane 110 conforms to the ear cavity 182 (or portion of the ear cavity and/or any other cavity or surface being scanned). For example, the medium 120 may be inserted into the membrane 110, so that membrane 110 conforms to the cavity being scanned. At this point, scanner element 105 may scan the interior surface of the inflatable membrane 110 which when inflated with the medium 120 conforms to the ear cavity 182. The scanner element 105 may move within the membrane 110 to scan the interior surface of membrane 110. In this way, scanner element 105 may scan the interior surface of the membrane 110 and thus ear cavity 182. The scanner element 105 may generate a 2D image of the inflatable membrane approximating a snap shot of the anatomical cavity. Each pixel of the 2D image is then associated with distance information obtained during a scan, that is the distance from the scanner element 105 to the scanned portion of the membrane. The combination of the 2D image and distance information for each pixel of the 2D image corresponds to 3D data (for example, a 3D surface representative of the scanned cavity). In some implementations, the distance information determined from scanning data can correlate to groups of pixels, instead of a single pixel, on the 2D image.

Medium 120 may be a liquid, a dissolved gas, a gel, a hydrogel, and/or any combination of the four. The medium 120 may include additives dissolved into, or suspended in, the medium 120 to provide properties, such as selective absorption where one or more wavelengths of light are absorbed more than one or more other wavelengths. To illustrate, medium 120 may include a colored dye, suspension, a luminescent substance, and/or a fluorescent substance (and/or any other material having selective wavelength properties). The medium may also contain a bio-neutralizing, anti-microbial, or anti-oxidizing agent to improve the shelf life of the medium as well as a buffering agent to improve the stability of the medium. Moreover, the selective wavelength properties may, as described further below, allow 3D scanner and/or processor 190 to determine the shape of, distance to, and/or other properties of the scanned interior surface of membrane 110.

The inflatable membrane 110 may be implemented as any viscoelastic, elastic, plastic, and/or any other material that may be inflated to conform to the cavity, when the membrane 110 is inserted and inflated with medium 120. When the cavity corresponds to an ear canal, membrane 110 may have an inflated 3D shape and size that is substantially adapted to the ear cavity, although the membrane 110 may be used with other cavities and forms as well including a stomach, an esophagus, a bladder, and so forth. The membrane 110 may also include, or be coated with, a material to make the membrane fluoresce in the presence of white light, light of a particular wavelength, or a range of wavelengths, as further described below. In some implementations, the inflatable membrane may have a balloon-like shape with an opening, an interior surface, and an exterior surface. In some implementations, scanning the interior membrane 110, rather than the ear cavity directly, may reduce (if not eliminate) the interference caused by artifacts, such as ear hair, wax, and the like, and may thus improve the accuracy of the cavity measurement scan.

Figure 1D:
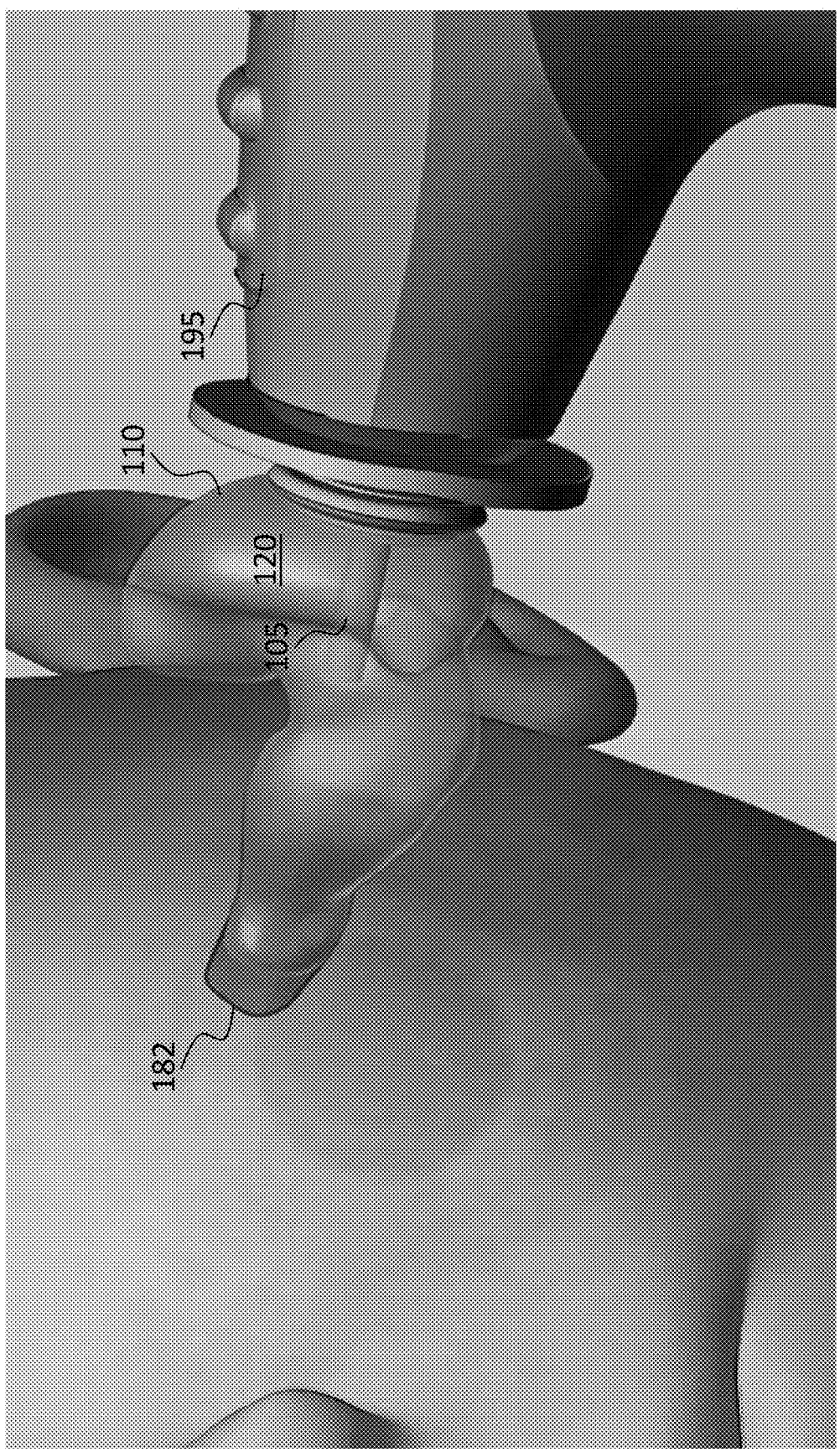

FIG. 1D depicts scanner element 105 after the scanner element has moved towards the opening of the cavity as part of the cavity scanning process. While scanning, scanner element 105 may scan one or more portions of the interior surface of the membrane 110, and element 105 may move within the membrane (and ear cavity 182) to image some (if not all) of the inner membrane 110/cavity 182. The scanner data collected by 3D scanner 195 may then be provided to one or more processors, such as computer 190 and/or a cradle-like device including an intermediary processor, to form a 3D surface or impression representative of the cavity as depicted at FIG. 1B, although some (if not all) of the processing may be performed by a processor contained in the 3D scanner 195 as well.

Figure 1E:
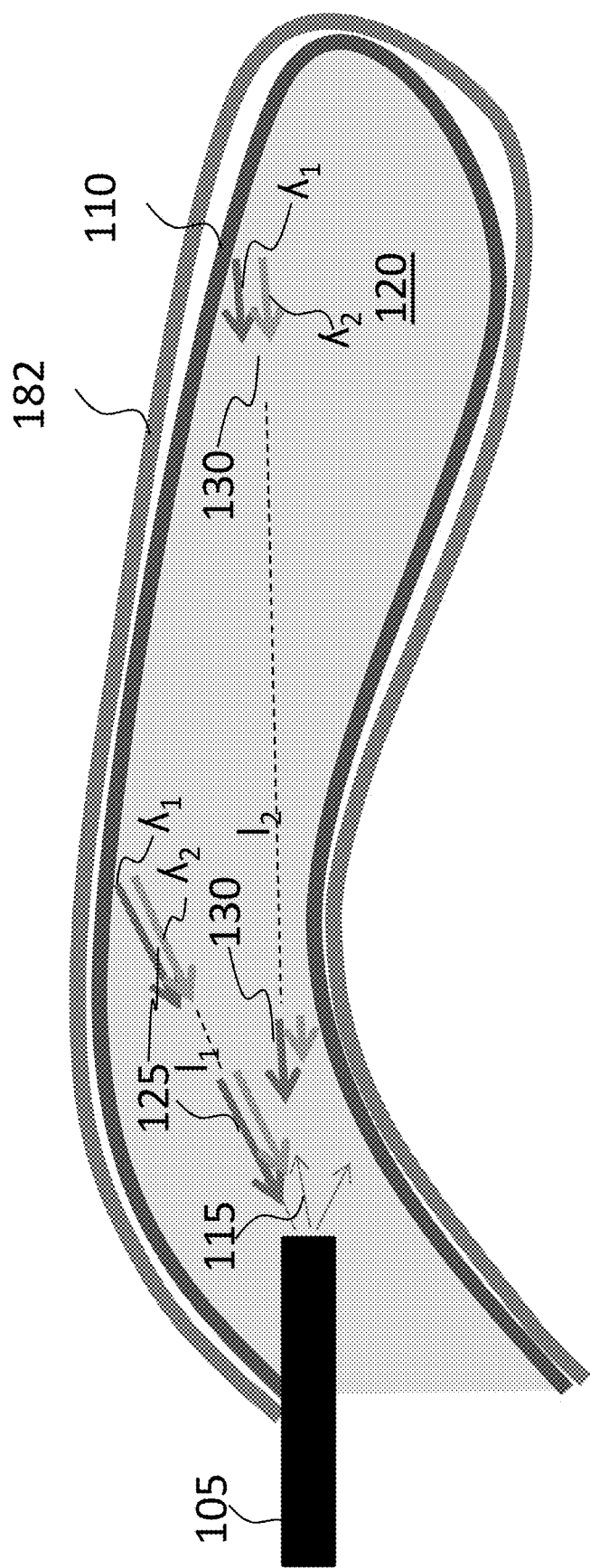
FIG. 1E shows a block diagram of a tip portion of the 3D scanner of FIGS. 1A, C, and D.

FIG. 1E shows a block diagram of the tip portion of 3D scanner 195 and, in particular, scanner element 105, inflatable membrane 110, and medium 120. The 3D scanner 195 and/or the scanner element 105 may include at least one light source, such as a light emitting diode, for emitting light 115 into the inflatable membrane 110, including medium 120. The scanner element 105 may also collect and/or detect light 125 and 130 that is emitted from fluorescent material in, or on, the inflatable membrane 110. The light 115 emanating from scanner element 105 may comprise light used to excite the fluorescent material in, or on, the inflatable membrane 110. Further, light from the fluorescent material in, or on, the inflatable membrane 110 may be referred to as "fluoresced" light, i.e., light resulting from the interaction of the fluorescent material with the light from scanner element 105.

The inflatable membrane 110 may include a fluorescent material, such as one or more fluorescent dyes, pigments, or other coloring agents. The fluorescent material can be homogenously dispersed within the inflatable membrane 110, although the fluorescent material may be applied in other ways as well (for example, the fluorescent material may be pad printed onto the surface of the inflatable membrane). The fluorescent material may be selected so that the fluorescent material is excited by one or more wavelengths of light 115 emitted by the scanner element 105. Once the fluorescent material is excited by light 115, the fluorescent material may emit light at two or more wavelengths $\lambda_1$, $\lambda_2$, or a range of wavelengths. For example, wavelength $\lambda_1$ may represent a range of wavelengths associated generally with red, although wavelength $\lambda_1$ may be associated with other parts of the spectrum as well.

As the two or more wavelengths 125 transmit back through the medium 120, medium 120 may absorb one or more of the wavelengths of light $\lambda_1$, $\lambda_2$ to a greater degree than one or more other wavelengths of the light. The medium 120 used in the system 100 may also be selected to optimally and preferentially absorb one or more of the wavelengths or a range of wavelengths of light from the fluorescent material of the inflatable membrane. By selecting an absorbing medium that complements the fluorescent material, the scan data collected by the 3D scanner may be more accurate.

When the tip portion 100 of 3D scanner 195 is inserted into ear cavity 182, 3D scanner 195 may pump (or insert in other ways) medium 120 into inflatable membrane 110 until the inflatable membrane 110 conforms to the surface of the cavity 182. Once the inflatable membrane 110 is fully inflated, 3D scanner and/or scanner element 105 may include a light emitting diode that generates light 115. Light 115 may travel from the scanner element 105, through medium 120, and excite the fluorescent material on, or in, a portion of the inflatable membrane 110. The light emitted from the fluorescent material on, or in, the inflatable membrane 110 may include at least two wavelengths of light. One of the wavelengths of light or some ranges of wavelengths of light emitted by the fluorescent material may be selectively absorbed by the medium 120. The light $\lambda_1$, $\lambda_2$ or ranges of light, may then be received by the scanner element 105, and the ratio of the intensities of light $\lambda_1$, $\lambda_2$ or the ratio of the integral area of light found under specific ranges may be measured and recorded by 3D scanner 195 and/or processor 190 to determine a distance from the scanner element 105 to corresponding surface of the membrane 110. The scanner element 105 may move throughout interior of membrane 110 to scan various portions of the surface of the membrane 110 and receive the fluoresced wavelength of light 125, 130 in order to collect data that can be used by the 3D scanner 195 and/or processor 190 to form 3D surface representative of the cavity. Alternatively, or additionally, the scanner element 105 may include optical, electronic, or mechanical components for focusing and directing the light used to excite the fluorescent material. Although the scanner element 105 may include one or more components, such as one or more light emitting diodes, optics, lenses, detectors/CCDs/CMOS sensors, and the like, one or more of these components may be located in other portions of the 3D scanner (for example, a fiber may carry light 115 to scanner element 105).

Figure 1F:
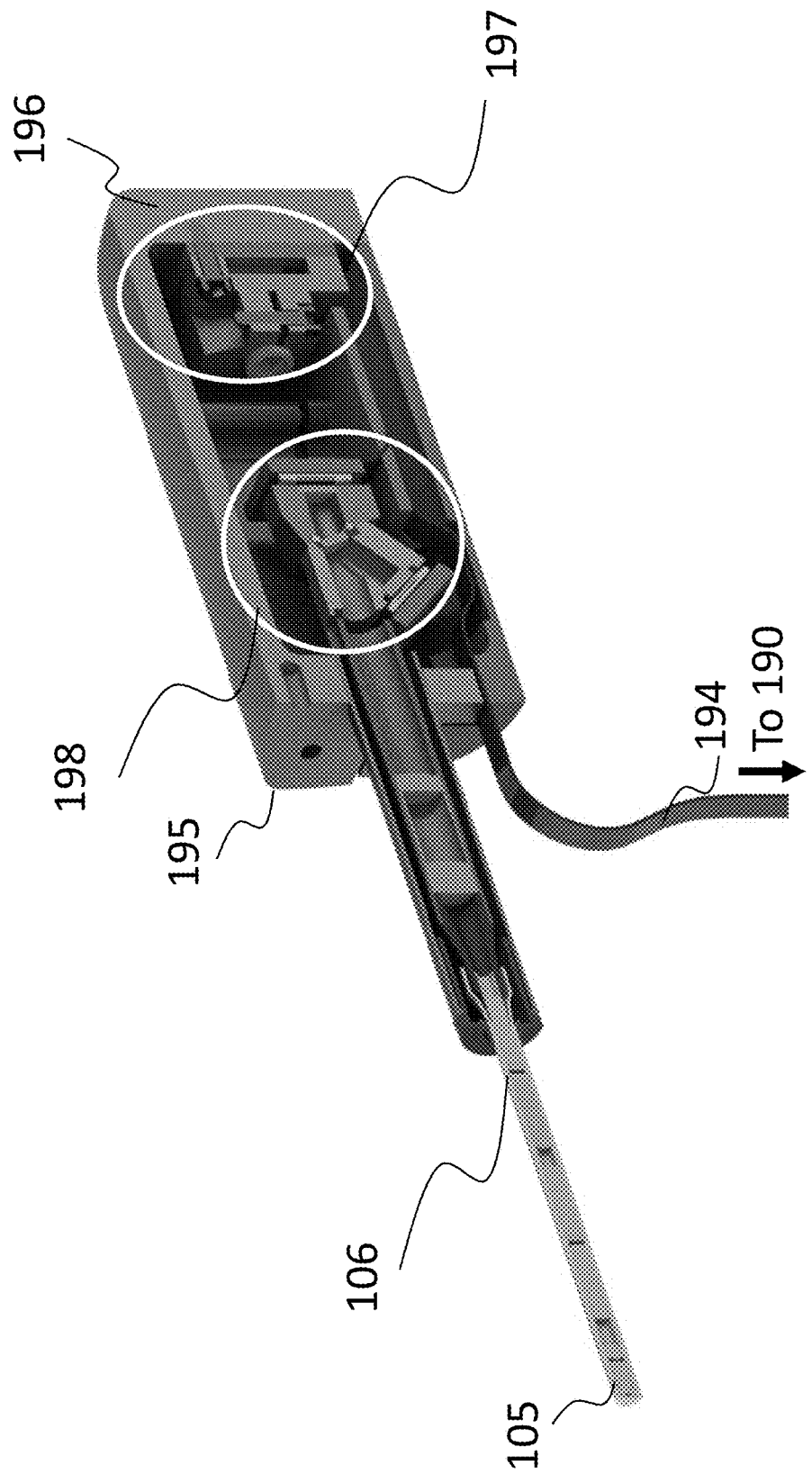
FIG. 1F depicts an example implementation of portions of the 3D scanner.

FIG. 1F depicts an example implementation of the 3D scanner 195 front-end, in accordance with some example implementations. The 3D scanner 195 may have a shroud 196 that houses an illumination component 197 and a sensing component 198. A cable 194 can connect the 3D scanner to the processor 190. Connected to the shroud 196 of the 3D scanner is the scanner element 105 (also referred to as a scope), which includes lenses 106 to focus light. The illumination component 197 produces light that excites the fluorescent material in the inflatable membrane, as well as light that may allow for general viewing of the cavity being scanned and the area around the cavity, such as when locating an area of interest. The light generated by the illumination component 197 for general viewing may be white light generated by one or more light sources, such as one or more light emitting diodes. The light generated by the illumination components 197 for excitation of the fluorescent material in the inflatable membrane may be blue light generated by one or more light sources, such as one or more light emitting diodes. The sensing component 198 may include one or more of a mirror, a beam-splitter, a filter, and/or multiple detectors. Each detector sends data to the processor 190 through the cable 194. The data from the one or more detector may be combined, multiplexed, or otherwise processed before it is sent through the cable 194. The processor 190 may send commands, such as illumination, scanning, or focusing instructions, to the front-end of the 3D scanner through the cable 194. The configuration of the components of the front-end of the 3D scanner shown in FIG. 1F is a representative configuration. The 3D scanner may have an illumination component 197, sensing component 198, scope 105, and processor 190 in other configurations suitable for scanning a cavity, such as an anatomical cavity.

Referring again to FIG. 1D, to determine distance from the scanner element 105 and a corresponding surface of the interior of membrane 110, the ratio of the intensity of two or more wavelengths or ranges of wavelengths may be used. Specifically, the intensity of the light emitted by the fluorescent material may be measured and recorded for at least two wavelengths, $\lambda_1$, $\lambda 2$, or ranges of wavelengths, one of which is the wavelength, or wavelength range, that is preferentially absorbed by the absorbing medium. The ratio of the intensity of two or more wavelengths, or ranges of wavelengths, at least one of which is preferentially absorbed by the absorbing medium, allows the 3D scanner 195 and/or processor 190 to calculate the distance between the fluorescent material of the inflatable membrane 110 and the distal tip of the scanner element 105 that receives the light 125, 130 from the fluorescent material. The light 115 from the scanner element 105 may scan the inner surface of the membrane 110 by illuminating points or areas on the inflatable membrane 110 in a sequential manner, so that an array of ratios of intensities of the wavelengths, and thus distances, corresponding to points on the inflatable membrane 110 can be created. As noted above, the scanner element 105 may move within the membrane 110 to allow illuminating portions along some, if not all, of the entire inner surface of the membrane 110.

The 3D scanner 195 may include a spectrometer to measure intensities for the two or more wavelengths, or ranges of wavelengths, of light from the fluorescent material. The wavelengths of light that can be compared include red light (such as light with wavelength ranging from about 620 to about 750 nanometers (nm)) and/or green light (such as light with wavelength ranging from about 495 to about 570 nm). Additionally or alternatively, the intensity of other wavelengths of light can be measured and compared, such as any combination of violet light (approximately 380 to 450 nm), blue light (approximately 450 to 495 nm), green light (approximately 495 to 570 nm), yellow light (approximately 570 to 590 nm), orange light (approximately 590 to 620 nm), and/or red light (620-750 nm). The spectrometer can include one or more detectors (for example, a charge coupled device, CCD, or a complementary metal-oxide semiconductor, CMOS) to measure the intensity of light and/or components to select the wavelengths to be measured (for example, one or more of a grating, a beam splitter, or a filter).

The 3D scanner 195 may also measure the intensity of one or more wavelengths or ranges of wavelengths of light from fluorescent material embedded in, or on, the inflatable membrane as a function of the degree of inflation of the membrane. That is to say, the inflatable membrane can be inflated to multiple levels of inflation while inside of an anatomical cavity, and measurements of the intensity of one or more wavelengths or ranges of wavelengths of light emitted from fluorescent material embedded in, or on, the inflatable membrane can be recorded and used to determine at least a 3D image or a surface topography of the anatomical cavity corresponding to the one or more levels of inflation. In the case of the human ear, particularly the aural canal, the size of the canal and compliance of the tissue in the canal can be determined, and the location of anatomical features, such as the bone-cartilage junction, can be found. Knowledge of the shape, compliance, and location of anatomical features can be used to create a device that provides better sound transmission, more comfort to a device user, or for the development of device materials. In some example implementations, the membrane 110 may be dynamically inflated to different pressures to enable the 3D scanner 195 to better scan certain anatomical features, such as the bone-cartilage junction and the like. This may be aided by asking the patient to move her anatomical features, for example by chewing, during the scan, and by observing changes in measurements as a function of this anatomical feature displacement. In this way, an earpiece, hearing protection, or hearing aid may be made that provides better sound transmission, sound protection, or comfort to a wearer.

The 3D scanner 195 may, as noted above, excite points or portions of the inflatable membrane in a sequential manner to obtain data that allows for the determination of the shape and mechanical properties, such as compliance, of the anatomical cavity surrounding the inflatable membrane. These properties can also be determined statically or dynamically as a function of time. The scan method and path, or sequence of points selected by the user or the system, can be chosen to improve accuracy, speed, or repeatability of the measurements made by the system. For example, 3D scanner 195 including the scanning elements 105 may be configured to allow scanning in a variety of methods and patterns to obtain as accurate a rendering of the anatomical cavity as possible. Such methods and scan patterns may include a hub-and-spoke pattern, a spiral pattern, a left versus right cue pattern, and/or any other method or pattern.

In the case of scanner element 105, fluorescent imaging through medium 120 may, as noted, selectively absorb one wavelength, or range of wavelengths, of light over another, and this selective absorption may be used to determine depth from scanner element 105 to the fluorescent membrane 110. This depth measurement may, as noted, be based on a ratio of the absorbed-to-transmitted wavelengths or ranges of wavelengths of light. Moreover, a processor may correlate the depth measurement to the corresponding scan data/images. For example, a portion of the 2D scanner image of the fluorescent membrane 110 may be correlated to a depth measurement determined from the ratio of the absorbed-to-transmitted wavelengths of light. In this way, the 2D scanner data/image is processed into a 3D image or surface.

Use of the Inflatable Membrane and Medium in 3D Scanning

As shown in FIG. 1E, when creating a 3D rendering of an anatomical cavity, the inflatable membrane 110 is substantially full of medium 120. Depending on some of the materials properties of the inflatable membrane 110, the shape of the membrane, and its insertion level into the cavity, the degree of inflation (e.g., the pressure applied), the inflatable membrane 110 may substantially conform to the shape of the anatomical cavity 182. The scanner element 105 can direct light 115 that impinges the inflatable membrane 110, and excites fluorescent material in or on the membrane to emit light 125, 130, with at least two distinct wavelengths, $\lambda_1$, $\lambda_2$, or ranges of wavelengths. As described above, 3D scanner 195 can create a 3D rendering of the anatomical cavity, can calculate certain mechanical properties of the anatomical cavity 182 when the inflatable membrane 110 is inflated to one or more pre-set pressures and scanned at each pressure, and/or can approximate the location of anatomical features, such as those that exhibit a change in modulus of the tissue of the anatomical cavity wall. To accommodate these and other use modes, the inflatable membrane 110 can have certain characteristics.

In some implementations, the inflatable membrane may contain a fluorescent material, such as a dye or pigment, that returns an image of fluoresced light when illuminated with visible blue or UV (ultra-violet) light. In other implementations, the inflatable membrane may contain a fluorescent dye that returns an image when illuminated with white light. Some implementations may include an inflatable membrane that contains a fluorescent dye that returns an image when illuminated with light that is not visible to the naked eye, that is to say light has a wavelength that is outside the range of about 390 to 700 nm. In implementations where the inflatable membrane contains a fluorescent material that returns an image of fluoresced light when illuminated with visible blue light, the membrane can fluoresce red and green light. Alternatively or additionally, the membrane can fluoresce in any combination of two or more wavelengths, or ranges of wavelengths, of light in response to illumination with blue or white light. In such implementations, there may be a wavelength, band of wavelengths, multiple wavelengths, or multiple bands of wavelengths of illuminating light, such that the spectrum of the fluoresced light emitted in response to the illuminating light may not change by more than about 0.5% over the length of the inflatable membrane. For example, if the inflatable membrane fluoresces red and green light in response to illumination with visible blue light, the ratio of red to green fluoresced light may not vary by more than about 0.5% over the length of the membrane, more than 1.0%, or more than 2.0% over the length of the membrane. In implementations where the inflatable membrane fluoresces red and green light, the absorbing medium can be a red fluid that preferentially absorbs the green light.

Because of the dependence of the 3D scanner on light detection to provide data from which the system generates distance information, and in turn a 3D surface model of a cavity, light should be able to travel through medium with as few interruptions as possible. Interruptions may include impurities in the medium, such as dust or particulate matter, or bubbles of air or other gases. The description below includes methods, apparatus, and systems that provide scanner configurations that may minimize gas bubbles in the medium, in accordance with some example embodiments.

Disposable and Reusable Components in the Scanning System

The user may receive a scanner with a scanner housing that may enclose components, including the light generating and detecting components, as shown in FIG. 1F. The scanner housing may also enclose a motor for moving absorbing medium into and out of the inflatable membrane by compressing and expanding a container holding the absorbing medium. The medium container may be any suitable compressible container, for example a bellows container or a syringe. The scanner housing may enclose the container, as well. The inflatable membrane may be attached to parts of an earpiece that attach to the scanner housing, for example using an O-ring and other fittings.

The earpiece may be for inserting into a patient's ear during scanning procedures. The earpiece may include numerous components. One of the earpiece components may be a fitting that receives absorbing medium and inserts the medium into the inflatable membrane. Another component of the earpiece may be the scanning element that illuminates and receives light from the interior of the inflatable membrane during scanning. The earpiece may also include one or more components that interface with the optical components of the scanner, for example the light source and the spectrometer. Additionally, the earpiece may have components that connect the earpiece to the scanner housing.

In some implementations, a scanner may be provided to a user as one or more components, some of which may be disposable and/or reusable components. The disposable component may be disposed after, for example, each scan, each orifice scanned, each patient, after a predetermined number of scans, or any combination thereof. For example, when scanning a patient's ears, the disposable component may include the inflatable membrane, and that may be disposed after taking a scan on a single ear, a pair of ears, and/or other quantities of ears. The reusable component may be reused one or more times before disposal. For example, a reusable component may be used with multiple patients, either over a set time-period or for a predetermined number of scans or patients. For example, the absorbing medium may be used with multiple patients, and so the container and tubing that hold and transport the absorbing medium in the scanner may be reusable. Since the medium contacts only the fluid storage container and the inside of the inflatable membrane, the medium may retain purity for a prolonged amount of time, with for example, careful storage procedures and/or careful exchange of the disposable components of the scanning system.

Figure 2A:
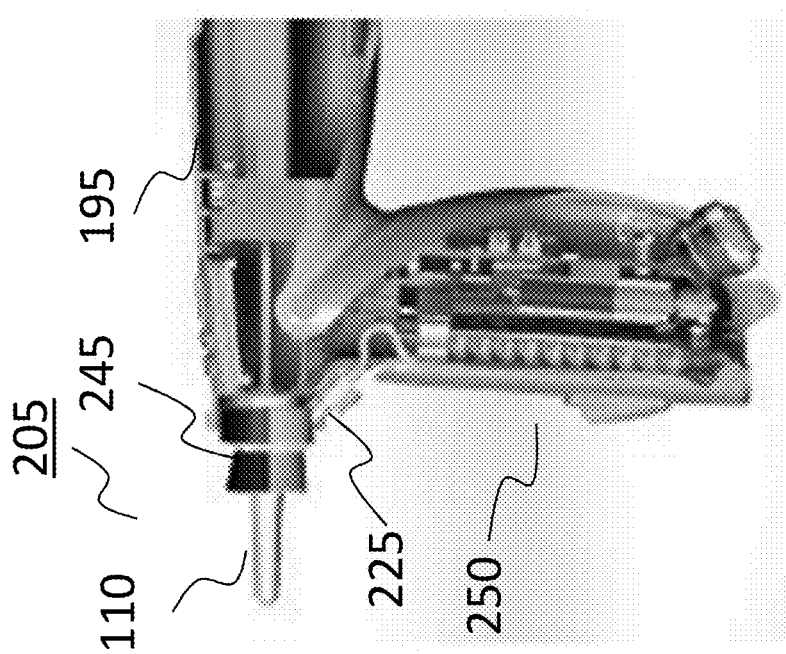
FIGS. 2A-2C depict an example implementation of a 3D scanner with disposable and reusable portions.

In an exemplary scanner 195, shown in FIG. 2A, the earpiece 205 that is inserted into a patient's ear may be implemented as a disposable component. Conversely, the container and tubing 250 that supply absorbing medium, as well the absorbing medium itself, may be a reusable component.

The earpiece 205 and the medium container and tubing 250 may be joined prior to use in the scanner 195, as shown in FIG. 2A. Once the earpiece 205 and the medium container and tubing 250 are joined, they form a substantially closed system. In the substantially closed system, any air or other gas that was present in the system (e.g., inside the earpiece 205, particularly the inflatable membrane 110) prior to joining may be trapped. The trapped gas may pose a problem if it is not confined to a location away from the earpiece during scanning, for example through priming. Configurations for confining trapped gas, as well as methods for confining the gas, are described in greater detail below.

Figure 2C:
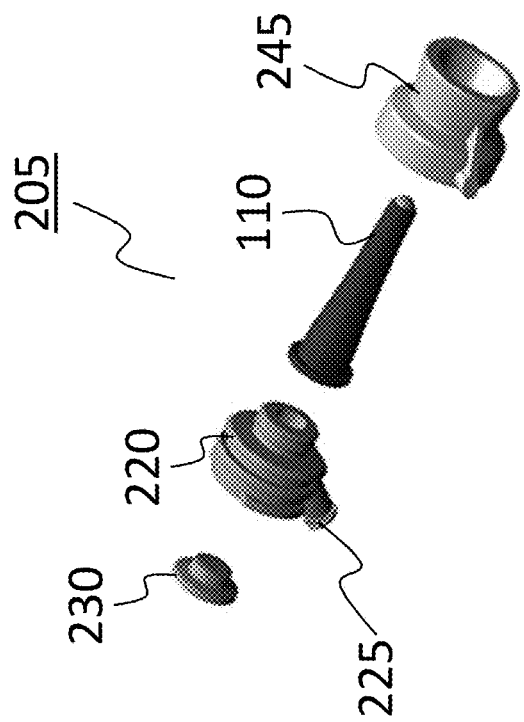
Figure 2B:
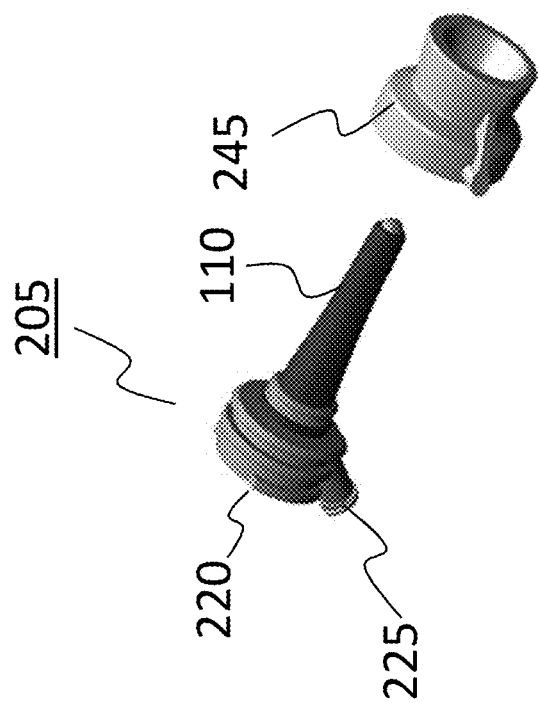

Further with respect to FIG. 2A, earpiece 205 may include inflatable membrane 110, a connector 225 to the medium container and tubing, and/or an attachment fitting 245. The fitting 245 may serve the following purposes: acting as an attachment fitting to securely fastening the earpiece 205 to the scanner; securing the membrane 110 to the housing 105; acting as an inflation guide for the membrane; encouraging conformation of the membrane to the cavity (e.g., ear canal); and/or assisting the operator in correctly placing the scanner with respect to the ear or any other area surrounding a cavity. FIGS. 2B and 2C depict the attachment fitting 245 removed from the earpiece 205 to better show other parts of the earpiece.

As mentioned above, the earpiece 205 may be disposed of after a relatively short time, for example, after each scan or after scanning each patient. An advantage of disposal is that the inflatable membrane 110 may avoid cross-contamination between patients. Additionally, the earpiece 205 may be received by the user in a dry condition. A dry condition means that the absorbing medium has not been in contact with the membrane 110. The longer the membrane 110 is able to be in a dry condition, the longer shelf life the system (e.g., disposable component) may have, as the dry condition extends the lifetime of the absorbing medium.

Although some of the examples refer to some of the components as disposable or reusable, the components may intended for long-term repeated use or may be any combination of disposable and/or reusable.

In FIGS. 2B and 2C, earpiece 205 is shown with a main body 220, a connector 225 to the container and tubing, the inflatable membrane 110, and a septum 230 for aligning and/or guiding light generated by the optics within the scanner 195. The septum 230 may guide a scope during alignment into the ear canal. The connector 225 may include a simple pressure fitting or threaded fitting, such as a Luer fitting. The main body 220 may include an integrated valve that may be controlled by other parts of the scanner 195 to selectively permit flow of medium and/or gas into and out of the inflatable membrane 110 (for example, during the pumping described below to remove unwanted gas particles in the absorbing medium). Further, the earpiece 205 may have any suitable configuration to minimize the gas that is trapped inside of the earpiece 205. Configurations to minimize the gas trapped inside the earpiece 205 may include a design minimizing the volume of the interior of the earpiece 205. This, in turn, may help to minimize the gas trapped inside the inflatable membrane 110 once the earpiece 205, medium container, and tubing 250 join.

Figure 3A:
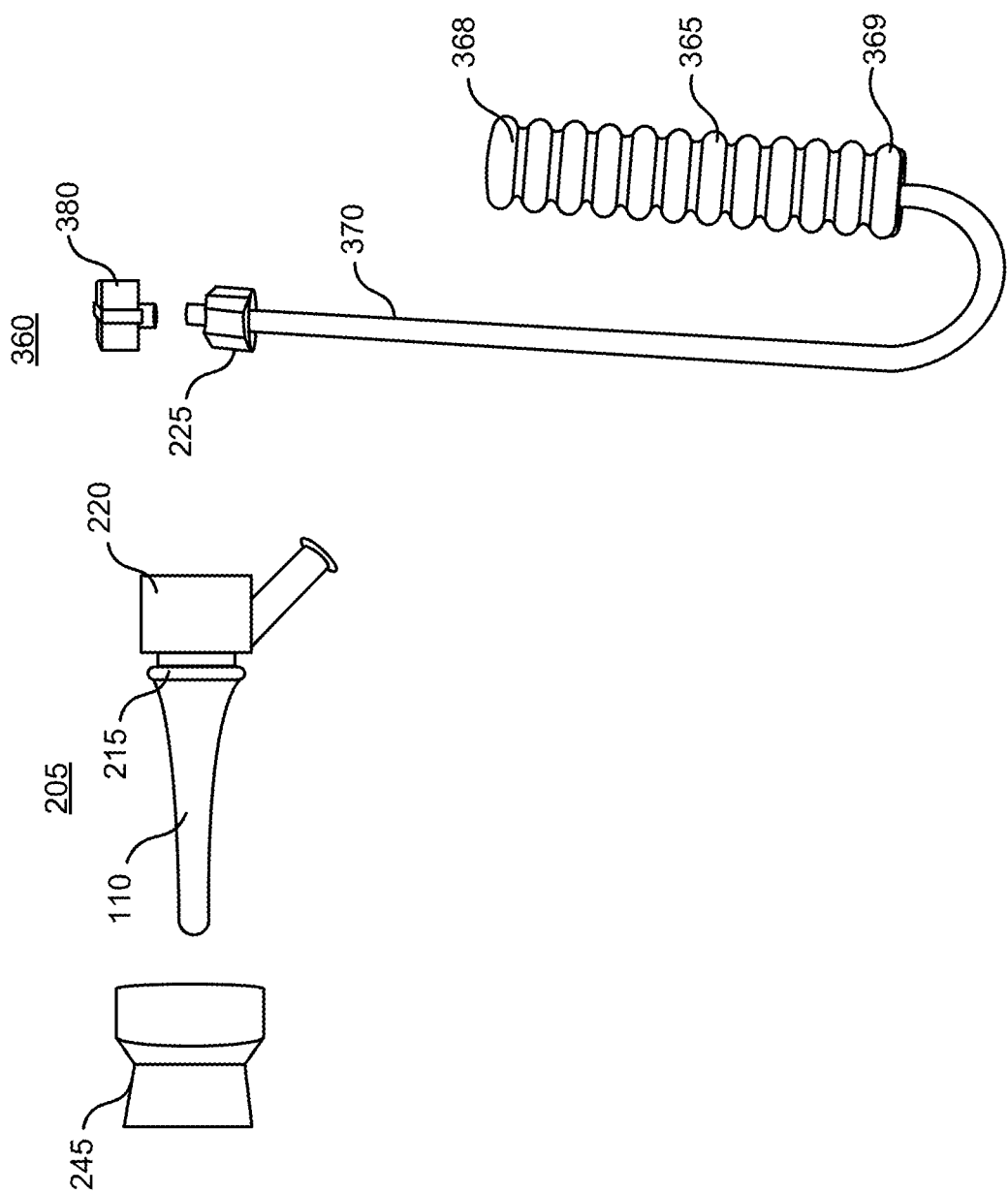
FIG. 3A depicts an exploded view of the disposable and reusable portions of the 3D scanner of FIG. 2A.

FIG. 3A depicts an exploded view of portion of the 3D scanner 195 of FIG. 2A. FIG. 3A shows an example of some of the components of a closed system for removing trapped gases from absorbing medium that is used in the inflatable membrane 110.

The system may include an earpiece 205 and an assembly 360 that may contain and transport the absorbing medium.

The earpiece 205 may include inflatable membrane 110, a main body 220, a connector 225 for coupling to a container 365 and tubing 370, and an O-ring 215 that prevents medium leakage from the inflatable membrane 110. The earpiece 205 may couple to the scanner housing via attachment fitting 245. When assembled, the attachment fitting 245 fits over the main body 220, compressing the O-ring 215 and the inflatable membrane to the main body 220. The attachment fitting 245 also joins the earpiece main body 220 to the scanner housing when the scanner is assembled.

The medium assembly 360 may include a medium container, or container, 365 and tubing 370. The medium container 365 has a top portion 368 and a bottom portion 369. The tubing 370 may connect to the medium container 365 at the bottom portion 369 of the medium container. The tubing 370 may couple the medium container 365 to connector 225. The connector 225 may join the tubing 370 to the main body 220 of the earpiece 205 when the closed system is being primed or when the scanner is in use. The connector 225 may be capped by a plug 380 when the medium assembly 360 is being stored, shipped, or is otherwise not in use.

During priming (also referred to as pumping) of container 365, the absorbing medium moves from the absorbing medium container 365 to the earpiece 205, specifically the inflatable membrane 110 of the earpiece. The air or other gas that may be present in the tubing 370, connector fitting 225, main body 220, and/or inflatable membrane 110 may need to be removed from scanning locations. In some implementations, such as that shown in FIG. 3A, due to the priming/pumping, this gas may collect at the top portion 368 of the medium container 365. Priming/pumping may involve moving absorbing medium through the closed system, from the absorbing medium container 365, to the inflatable membrane 110, and back, multiple times.

This movement of the medium may cause gas (for example, air bubbles and the like) which may be located in so called "crucial" portions of the closed system to be moved (for example to location 368), eliminated, or reduced. The so-called crucial areas refer to locations in the closed system where the presence of volumes of gas, for example, an air bubble, can adversely affect scanning by absorbing or scattering light generated during the scanning process, for example light generated by the scanning system or by fluorescent material in the inflatable membrane. Alternatively or additionally, the absorbing medium may, during priming/pumping, move slowly through the closed system so that gas has time to move away from a crucial portion of the system prior to scanning.

These methods for confining the gas trapped within the closed system may be collectively called priming, purging, and/or pumping. In some implementations, the closed system may include one or more semipermeable surfaces to allow trapped gases to escape during the priming. The semipermeable surface may be located at the container 365, as well as at other locations, such as the tubing 370, connector 225, and/or the like.

Figure 3B:
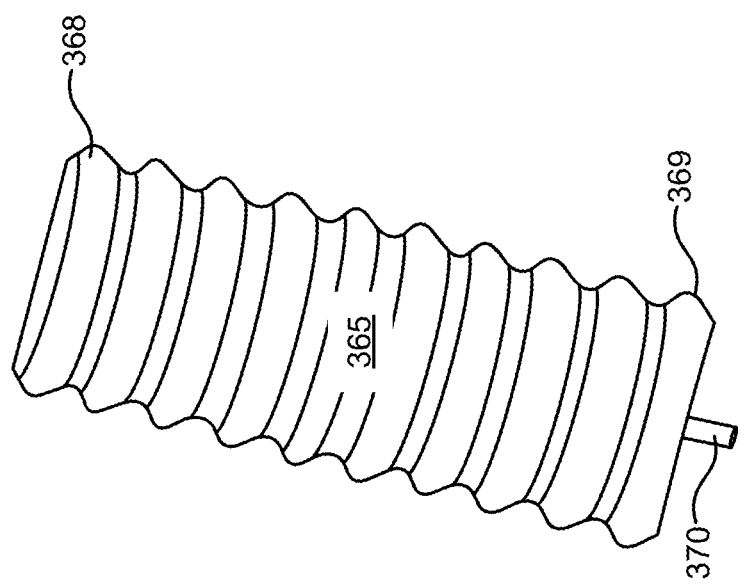
FIG. 3B depicts an example implementation of a bellows fluid container.

FIG. 3B shows an exemplary medium container 365 in more detail. The medium container 365 in FIG. 3B has a top portion 368 and a bottom portion 369, as well as tubing 370. The tubing 370 connects to the medium container 365 at the bottom portion 369.

In the embodiment shown in FIG. 3B, the medium container 365 is shown as a bellows or accordion container. Bellows or accordion containers may have ribbing that allows the container to collapse in a controlled manner when force is applied to one or both ends during the priming/pumping. Pulling one or both ends of a bellows or accordion container may also allow for controlled expansion of the container 365. Force may be applied to the top portion 368 of the medium container 365 in FIG. 3B. As the top portion 368 receives force, the contents of the medium container (e.g., absorbing medium, trapped volumes of gas) may move toward the bottom portion 369 and through the tubing 370. A pulling force on the top portion 368 may draw up absorbing medium and gas through the tubing 370 and the bottom portion 369 of the medium container 365. The medium container 365 may have a volume and length that allows trapped gas to be confined to the top portion 368 after purging or priming the closed system. The forces applied to the medium container 365 may prevent trapped gas from leaving the medium container 365 and/or tubing 370 when the medium container 365 is collapsed during scanning. The forces applied may be predetermined.

Though the medium container 365 is shown and described as a bellows or accordion container, it can be any type of container that can collapse in a controlled manner. Control may be achieved through applied physical forces, electrical current, mechanical actuation, and the like. For example, the medium container 365 may be a syringe that is controllably collapsed or expanded using a motor.

Figure 4:
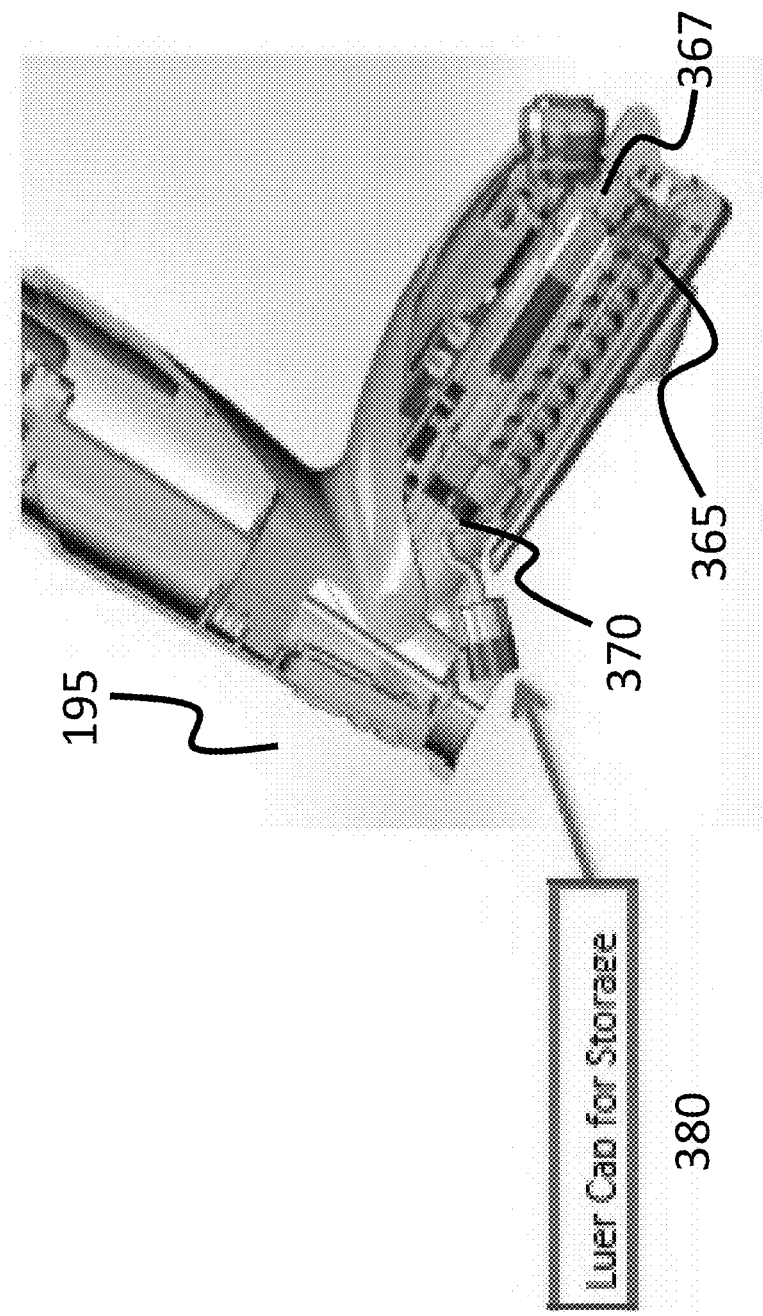
FIG. 4 depicts an example implementation of the reusable portion of the 3D scanner shown in FIG. 2A in a storage configuration.

FIG. 4 depicts a portion of scanner 195 (earpiece 205 is not shown). The scanner is depicted in a storage configuration. The scanner housing encloses the light producing and detecting electronics, medium container 365, tubing 370, and a compression motor (e.g., expelling assembly) 367. Tubing 370 may be capped with storage cap 380. The storage cap 380 may prevent absorption medium from leaking out of, or air from leaking into, the tubing during transport or storage.

Figure 5:
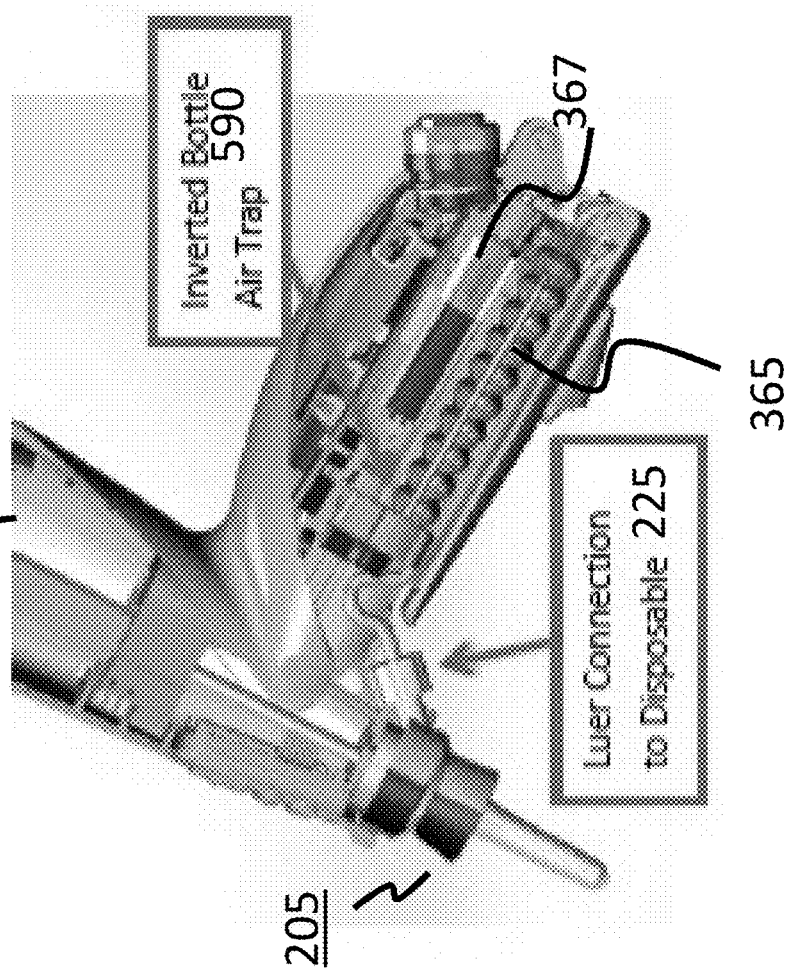
FIG. 5 depicts an example implementation of the 3D scanner shown in FIG. 2A connected to the disposable portion.

Once a user decides to use the scanner 195, he or she joins the earpiece 205 to the tubing 370 using a connection 225 after removing the storage cap 380, resulting in the scanner shown in FIG. 5. In the implementation shown in FIG. 5, the medium container 365 has an air trap 590. The air trap 590 may be at the top portion of the medium container 365, although it may be located at other locations along container 365 as well. Air trap 590 may provide, during the priming/pumping of container 365, a volume for air trapped in the closed system to go when the earpiece 205 joins with the tubing and medium container assembly. The air trap 590 may include a semipermeable membrane or other gas permeable surface that allows air and other gas to escape the medium container 365 as a relief mechanism.

As described above, a portion of the container 365 may be an air trap 590. The air trap 590 may be sized to confine the air or other gas in the system. When the compression assembly 367 pushes on the container 365, the gas in the system may remain in the air trap 590. Alternatively the gas in the system may move from the air trap 590, through the medium container 365, and into the tubing 370 without reaching the earpiece. In this way, by priming the system and using an air trap, the gas in the system may not form bubbles in the earpiece, affecting the accuracy of scan data.

Figure 6B:
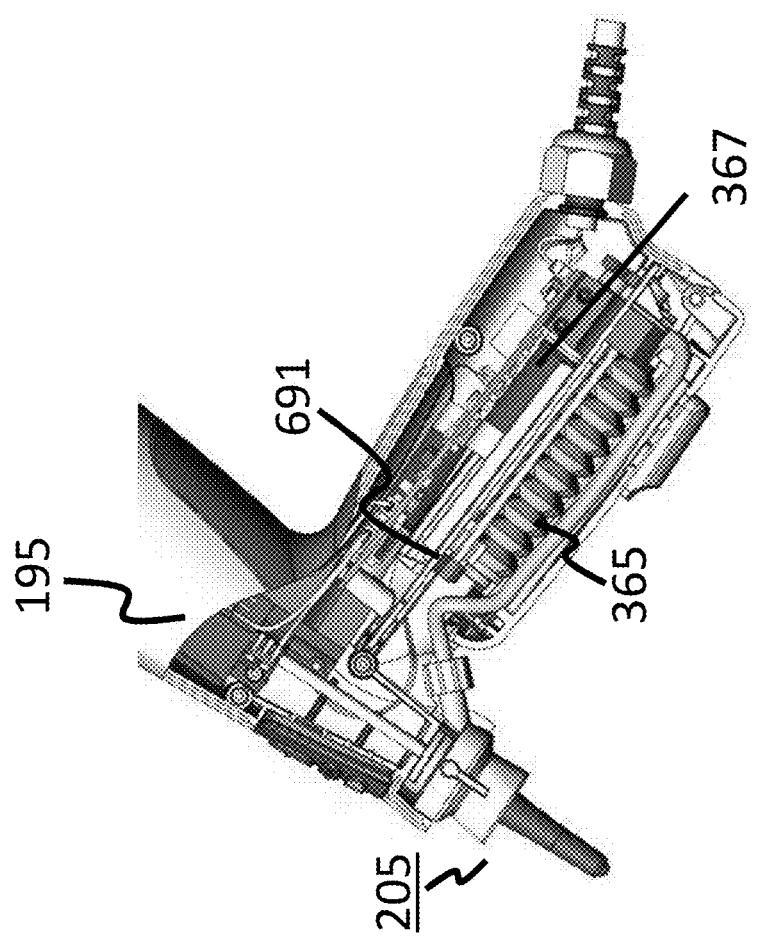

FIGS. 6A and 6B depict further views of the 3D scanner 195 shown in FIGS. 2A, 4, and 5. In FIGS. 6A and 6B, the compression assembly 367 is shown with a disc that applies pressure to the top end of the medium container (e.g., an advancing component) 691. The pressure disc 691 may be adjacent to the top end 368 of the medium container 365. The scanner 195 may receive input or instructions that cause the compression or expelling assembly 367 to move the pressure disc 691. The pressure disc 691 may be attached to, or fitted against, the top end 368 of the medium container 365. When the pressure disc 691 moves, the medium container 365 may contract or expand correspondingly. A rotational or linear movement means can cause the pressure disc 691 to travel within the scanner. For example, a long threaded screw may correspond to threads within the pressure disc 691, and as the long threaded screw rotates, the advancing component 691 may advance or retreat.

Figure 7C:
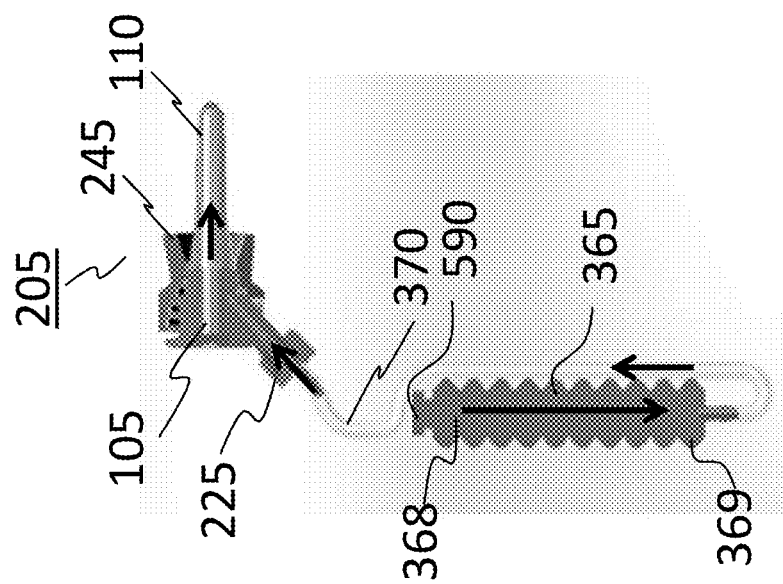
FIGS. 7B and 7C depict alternate views of the bellows fluid container and the disposable portion of the 3D scanner shown in FIG. 7A.
Figure 7B:
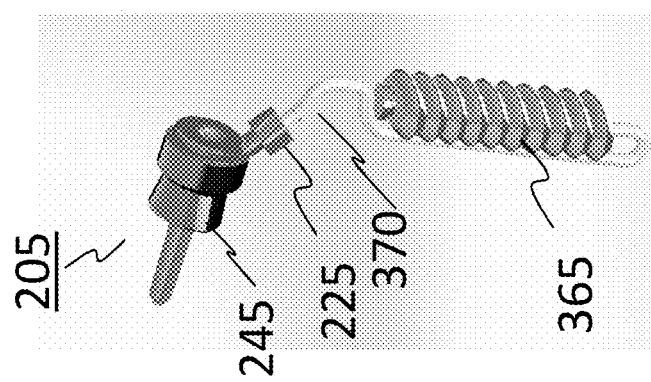

FIG. 7A depicts an alternate view of the 3D scanner 195 shown in FIGS. 6A and 6B. The scanner 195 in FIG. 7A includes an earpiece 205 with an attachment fitting 245 and a connector 225 to join the earpiece 205 to the tubing 370. The tubing 370 in the scanner is also connected to the bottom portion of a medium container 365. FIGS. 7B and 7C depict alternate views of the bellows medium container 365 and the earpiece 205 of the 3D scanner 195 shown in FIG. 7A. FIG. 7C is a cross-sectional view of the items shown in FIG. 7B, so that the relative positions of the components are shown. FIG. 7C shows a fluid path from the container to the earpiece 205, particularly inside the inflatable membrane 110.

Figure 8A:
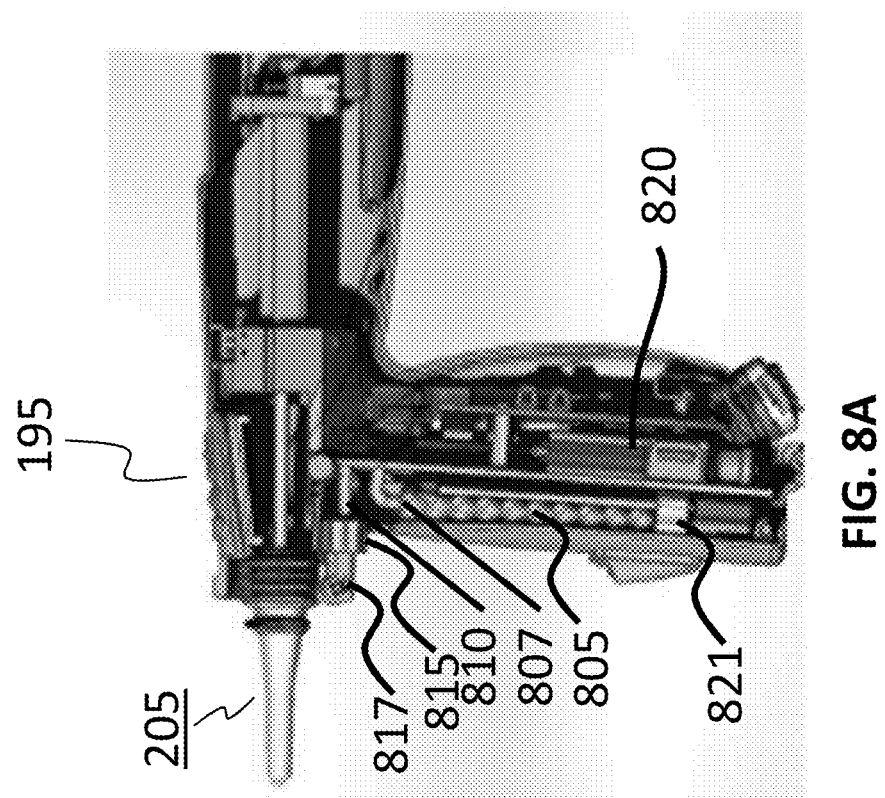

FIGS. 8A and 8B depict an example implementation of a 3D scanner 195 with an alternative configuration of the medium container 805. This implementation of a 3D scanner 195 includes an earpiece 205, a medium container 805 with a top portion 807 and a bottom portion, and a compression or expelling assembly 820 with a pressure disc (e.g., advancing component) 821. The bottom portion of the medium container 805 may be adjacent to and/or attached to the pressure disc 821. The top portion 807 of the medium container 805 connects to tubing 810 that terminates in a connector 815. The connector 815 may be a pressure fitting or a threaded fitting, for example a Luer fitting, and may connect to a mating connector on the earpiece 205. Adjacent to the connector 815 may be a gas release (e.g., a valve or opening) 817. The gas release (e.g., gas relief mechanism including a semipermeable membrane, relief valve, or the like) 817 may allow trapped air or other gas to leave the scanner system once the earpiece joins the tubing and medium container, with or without movement of the medium in the system.

The medium container 805 may surround a dip tube that attaches to the tubing 810 at the top of the container 807. The dip tube may extend down into the container part of the way, such as ⅓, ½, or ¾ of the way into the fully extended medium container. In these configurations, the compression or expelling assembly 820 and pressure disc 821 may compress the medium container 805 only so far so as to contact, but not deform, the dip tube. Alternatively or additionally, the compression or expelling assembly 820 and pressure disc 821 may compress the medium container 805 without the bottom of the medium container 805 contacting the bottom of the dip tube. As with the scanner 195 described above, the pressure disc may connect to a rotational or linear movement means (e.g., a stepper motor, a screw) that may move the pressure disc 691.

The configuration of the medium container 805 shown in FIGS. 8A and 8B may allow for air or other gas to rise to the top 807 of the container. Because the system draws medium from the bottom of the dip tube within the medium container 805, gas may be excluded from the volume of the earpiece 205. This exclusion of gas from the absorption medium delivered to the earpiece may help the scanner to obtain accurate data. Drawing out air or other gases that may be present in the earpiece 205 just after attaching it to the tubing and medium container may require priming or purging. As described above, priming or purging may involve the translation of medium in and out of the orifice assembly 205 one or more times prior to scanning.

Figure 9B:
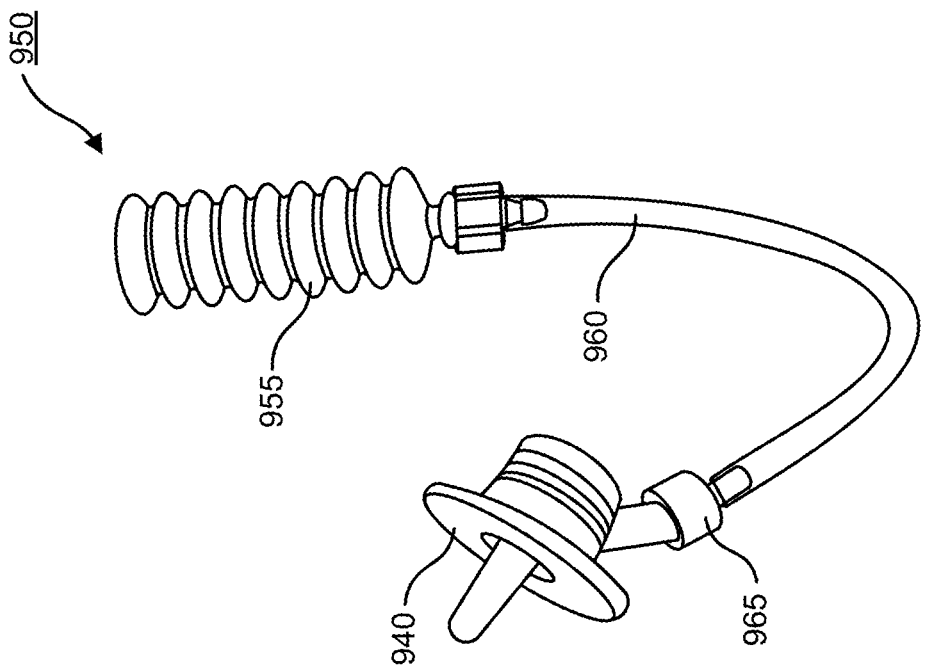
FIG. 9B depicts an implementation of a bellows fluid container.
Figure 9A:
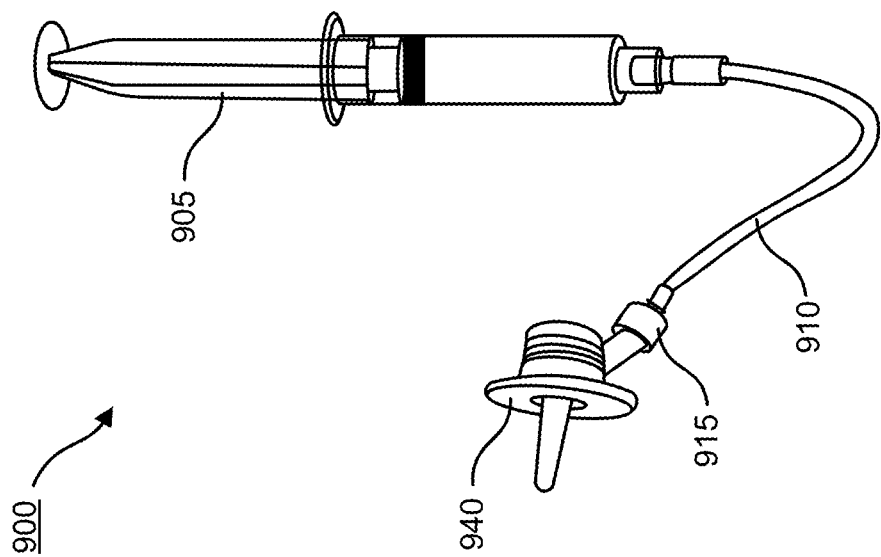
FIG. 9A depicts an implementation of a syringe fluid container.

FIGS. 9A and 9B depict example prototypes used in experiments to show the functionality of the concept of a disposable earpiece and a reusable length of tubing and medium container. One of the goals of the experiments was to demonstrate that a priming cycle could purge air from the critical component (e.g., the membrane) of a closed system. Another goal of the experiments was to show that priming could be completed while the scanning system was in a storage configuration.

The experiments were conducted to determine the number of purge cycles (e.g., priming) to remove air from a disposable earpiece system (e.g., orifice assembly) and to approximate the amount of absorbing medium loss per disposable earpiece use. In these experiments, water was used as a representative absorbing medium as the surface tension of water can represent a worst-case scenario for that materials characteristic, when comparing to the surface tension of other absorbing medium fluids. Each experimental set-up included an earpiece system (analogous to the earpiece 205) made of ABS (acrylonitrile butadiene styrene) that was 3D printed to have a 48 degree interface fitting with the medium providing assembly. Each earpiece system also had an inflatable membrane. Each inflatable membrane was expanded inside a representative volume that was the same for each test in the experiment. There were two types of medium containers tested, shown in FIGS. 9A and 9B. FIG. 9A depicts an implementation 900 of a syringe fluid container 905 used in the experiment, and FIG. 9B depicts an implementation 950 of a bellows fluid container 955 used in the experiment.

In FIG. 9A, the syringe fluid container 905 shown was a 10 ml syringe. The syringe 905 was connected to 5 inches (approx. 12.7 cm) of tubing 910. The tubing 910 shown had an inner diameter of 3/32 inches and an outer diameter of 5/32 inches. The tubing 910 ended in a connector 915 that interfaced with the earpiece system 940. In FIG. 9B, the bellows medium container 955 had approximately a 10 ml capacity. The bellows medium container 955 was connected to tubing of similar dimensions to that in FIG. 9A. The earpiece system 940 was similar in both types of tests associated with the set-ups shown in FIGS. 9A and 9B.

During the experiment, simulated medium flowed in purge cycles with the earpiece systems at an angle simulating the relative positions within a scanner in a storage configuration. In each set-up, the syringe 905 or bellows container 955 were moved appropriately to affect a purge cycle, and after each test, a new inflatable membrane was attached to each earpiece system 940.

A purge was defined as either maximal or minimal. A maximal purge caused full inflation of the inflatable membrane in the test set-up. Full inflation of the inflatable membrane in the test set-up was equivalent to inflation with approximately 8 mL of water. A minimal purge caused no or minimal inflation/stretching of the inflatable membrane and/or had minimal inflation cycles.

The experimenters found that there was approximately 0.1 to 0.2 mL of medium lost each time the earpiece was changed. The number of purge cycles required to fully purge the air using minimal inflation was 3-4, whereas when using full membrane inflation, the experimenters removed all air from the earpiece system in 1-2 purge cycles. The experimenters found that the syringe system allowed them to more accurately measure the loss in medium. They also found that the bellows container performed similarly to the syringe. In both experimental set-ups, it was noted that the ability to draw a vacuum (e.g., draw the air out of the earpiece by pulling back on the syringe or hyper-extending the bellows) helped to purge the system of gas.

Figure 10A:
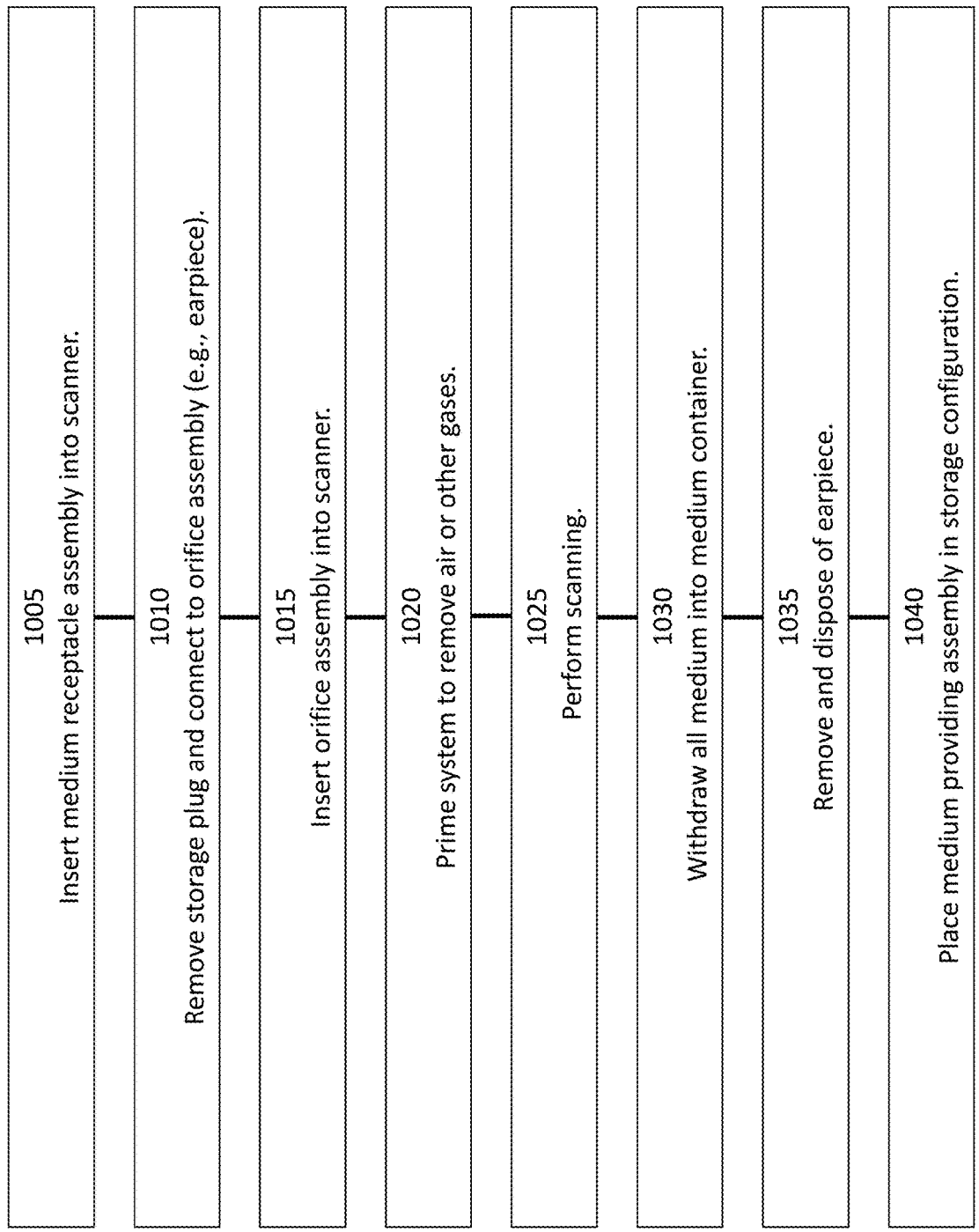
FIG. 10A depicts a method for using a closed system for scanning a cavity with reusable and disposable components.

FIG. 10A depicts a method for using a closed system for scanning a cavity with reusable and disposable components. The closed system may allow for changes in the absorbing medium, the absorbing medium container, and/or the scanner housing independent of changes in the earpiece.

When using a closed system for scanning a cavity with reusable and disposable components (e.g., with an earpiece and tubing attached to an absorbing medium container), a user inserts a medium container assembly that is in a storage configuration into scanner, as in 1005. This may include attaching portions of the medium container to pressure disc (e.g., an advancing member) of a compression assembly. The storage configuration of the medium container assembly (e.g., medium container and attached tubing) may include a plug or other stopper that prevents absorbing medium from leaving the container or any attached tubing.

Next, the plug or stopper is removed and the user or system attaches the earpiece (e.g., orifice assembly), as in 1010. As described above, the connector between the medium container and its attached tubing and the earpiece may be a simple pressure fitting or it can be a threaded fitting. In some implementations, the connector between the tubing attached to a medium container and the earpiece includes a Luer fitting.

Once the medium container and its attached tubing and the earpiece are connected, the orifice assembly is placed into the scanner by a user or portions of the system, as in 1015. Some configurations may allow for automated connection of the medium providing assembly and the orifice assembly, as well for automated insertion of those components into the scanner. Following this, 1020 indicates that priming of the system occurs. Priming may include the transport of air or other gas (e.g., bubbles, volumes of gas) in the system to a portion of the system where it will not interfere with scanning or give rise to erroneous data. A process for priming is depicted below with respect to FIG. 10B.

Once primed, the system or user can commence scanning of the anatomical cavity, as in 1025. At the conclusion of scanning, the system or user may operate the compression assembly to withdraw the absorbing medium into the medium container, 1030. After the absorbing medium is back in the medium container, as in 1030, the tubing and medium container (e.g., medium providing assembly) may be placed into a storage configuration, as in 1040, and the orifice assembly may be removed and disposed of, as shown in 1035.

Figure 10B:
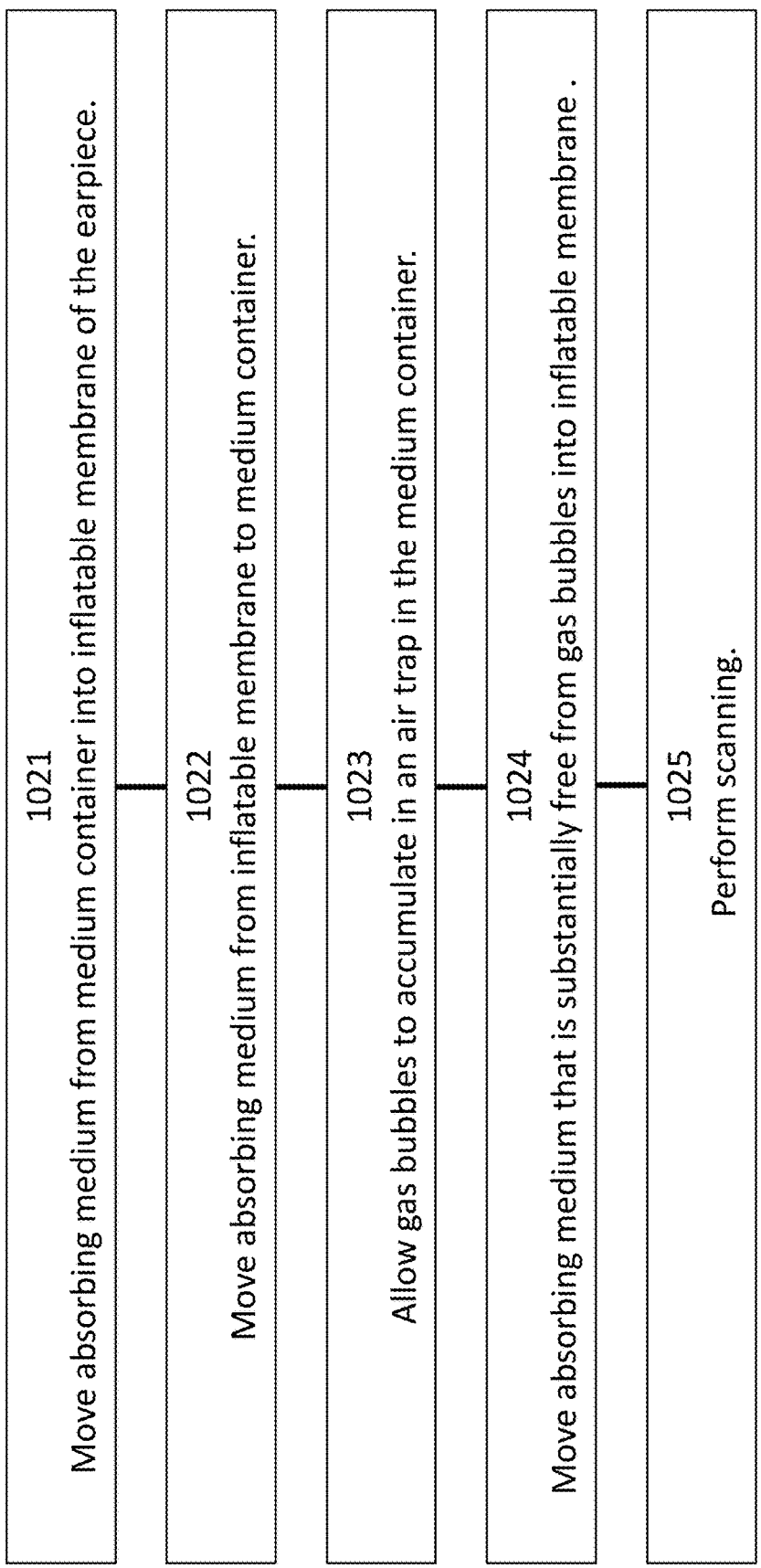
FIG. 10B depicts a method for priming a closed system for scanning a cavity.

An exemplary method of priming or purging a closed system for scanning an anatomical cavity is shown in FIG. 10B. Priming may be initiated by a user or the system to cause a movement of the absorbing medium from the medium container into the inflatable membrane of the earpiece, as in 1021. This is followed by the movement of absorbing medium from the inflatable membrane to the medium container, as shown in 1022. As shown in 1023, during the movement of absorbing medium into the medium container, gas bubbles accumulate in an air trap in the medium container. The absorbing medium can flow between the medium container and the earpiece more than once to remove gas bubbles from the bulk of the absorbing medium. When the user or system determines that the absorbing medium may be substantially free from gas bubbles, the gas-bubble-free absorbing medium may flow into the inflatable membrane, as in 1024, and then, as in 1025, the scanner can obtain scanning data.

Though the methods, apparatus, and systems are described herein with respect to an earpiece and scanning an ear canal, these methods, apparatus, and systems may be applied to any cavity or orifice assembly for scanning any suitable anatomical cavity. For example, the methods, apparatus, and systems can be used for scanning oral, nasal, renal, intestinal, or other anatomical cavities, and can involve assemblies designed for those anatomical cavities. Further, these methods, apparatus, and systems may be used with sensitive or fragile cavities that are not anatomical in nature, such as those made from brittle, pliable, or otherwise delicate materials. Additionally, although methods, apparatus, and systems are described herein with respect to removal of air and air bubbles from a closed system, these methods, apparatus, and systems may apply to removal of any gas or volume of gas from a closed system.

Without in any way limiting the scope, interpretation, or application of the claims appearing below, a technical effect of one or more of the example embodiments disclosed herein is reusability of certain components. Moreover, without in any way limiting the scope, interpretation, or application of the claims appearing below, a technical effect of one or more of the example embodiments disclosed herein is that the medium providing assembly may be used for multiple scans, including for multiple patients. In some implementations, the absorbing medium and medium providing assembly may be used for 10-15 scans or more. Furthermore, without in any way limiting the scope, interpretation, or application of the claims appearing below, a technical effect of one or more of the example embodiments disclosed herein is that the absorbing medium, and the system as a whole, may be more likely to be shelf-stable, as it can be shipped without contacting the inflatable membrane until just before scanning.

Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. In various example implementations, the methods (or processes) can be accomplished on mobile station/mobile device side or on the server side or in any shared way between server and user equipment/mobile device with actions being performed on both sides. The phrases "based on" and "based on at least" are used interchangeably herein. Other implementations may be within the scope of the following claims.

What is claimed:

1. A handheld apparatus comprising:
a handle;
an earpiece coupled to a fitting that receives an absorbing medium and transfers it into an inflatable membrane; and
an absorbing medium assembly disposed in the handle and configured to fluidly connect to the earpiece and provide the absorbing medium to the earpiece, the absorbing medium assembly comprising:
a medium container, with a top portion and a bottom portion, to contain the absorbing medium, the medium container comprising a gas trap to remove gas from the absorbing medium in the earpiece; and
a tube fluidly connected to the bottom portion of the medium container and coupled to the fitting, the tube configured for transferring the absorbing medium from the medium container to the earpiece,
wherein the absorbing medium is at least one of a liquid, a gel, or a hydrogel.

2. The apparatus of claim 1, wherein the earpiece further comprises a scanning element to scan an ear.

3. The apparatus of claim 1, further comprising: a compressor coupled to the absorbing medium assembly to compress and to expand the medium container.

4. The apparatus of claim 3, wherein the medium container is a bellows container that enables collapse in a controlled manner when compressed by the compressor.

5. The apparatus of claim 1, wherein a first end of the tube couples to the bottom portion of the medium container.

6. The apparatus of claim 1, wherein a first end of the tube couples to the top portion of the medium container.

7. The apparatus of claim 6, further comprising: a dip tube disposed inside the medium container to draw the absorbing medium from the medium container and to enable avoidance of one or more volumes of gas within the medium container, wherein the dip tube is fluidly connected to the tube.

8. The apparatus of claim 1, wherein the gas trap is located at the top portion of the medium container.

9. The apparatus of claim 1, further comprising: a gas relief valve configured to enable gas to escape from the apparatus.

10. The apparatus of claim 9, wherein the gas relief valve couples the earpiece and the absorbing medium assembly.

11. The apparatus of claim 9, wherein the gas relief valve is located adjacent to the gas trap.

12. The apparatus of claim 9, wherein the gas relief valve comprises at least one of a semipermeable surface or a valve.

13. A method comprising:
moving, by an absorbing medium assembly, an absorbing medium from a medium container disposed vertically in a handle of an apparatus into an inflatable membrane of an earpiece of the apparatus through a fitting,
wherein the absorbing medium assembly is configured to fluidly connect to the earpiece and provide the absorbing medium to the earpiece,
wherein the absorbing medium assembly comprises the medium container having a top portion and a bottom portion, the medium container comprising a gas trap located at the top portion to capture gas in the absorbing medium, and a tube fluidly connected to the bottom portion of the medium container and coupled to the fitting,
wherein the absorbing medium is at least one of a liquid, a gel, or a hydrogel.

14. The method of claim 13, further comprising: moving, by the absorbing medium assembly, the absorbing medium from the medium container into the inflatable membrane of the earpiece to enable one or more volumes of gas in the absorbing medium to accumulate in the gas trap.

15. The method of claim 13, further comprising: moving, by the absorbing medium assembly, the absorbing medium, after at least some removal of one or more volumes of gas from the medium container, into the inflatable membrane of the earpiece to enable inflation of the inflatable membrane.

16. The method of claim 13, further comprising: scanning an ear with a scanning element of the apparatus.

17. The method of claim 13, further comprising: a compressor coupled to the absorbing medium assembly to compress and to expand the medium container to enable removal of one or more volumes of gas from at least the earpiece.

18. The method of claim 13, further comprising: a dip tube disposed inside the medium container to draw the absorbing medium from the medium container and to enable avoidance of one or more volumes of gas within the medium container, wherein the dip tube is fluidly connected to the tube.

19. The method of claim 13, further comprising: a gas relief valve configured to enable gas to escape from a system, the system comprising the absorbing medium assembly and the earpiece.

20. The method of claim 19, wherein the gas relief valve couples the earpiece and the absorbing medium assembly.

21. The method of claim 19, wherein the gas relief valve is located adjacent to the gas trap.

22. The method of claim 19, wherein the gas relief valve comprises at least one of a semipermeable surface or a valve.

* * * * *